(12) United States Patent
Sung et al.

(10) Patent No.: US 10,538,569 B2
(45) Date of Patent: Jan. 21, 2020

(54) FUSION POLYPEPTIDE CONTAINING GLP AND IMMUNOGLOBULIN HYBRID FC AND USE THEREOF

(71) Applicant: GENEXINE, INC., Seongnam-si, Gyeonggi-do (KR)

(72) Inventors: Young Chul Sung, Seoul (KR); Se Hwan Yang, Seoul (KR); Mi Sun Byun, Bucheon-si (KR); Sang In Yang, Daegu (KR); Eun Ju Shin, Gyeonggi-do (KR)

(73) Assignee: GENEXINE, INC., Seongnam-si (KR)

( * ) Notice: Subject to any disclaimer, the term of this patent is extended or adjusted under 35 U.S.C. 154(b) by 0 days.

(21) Appl. No.: 15/538,784

(22) PCT Filed: Dec. 31, 2015

(86) PCT No.: PCT/KR2015/014542
§ 371 (c)(1),
(2) Date: Jun. 22, 2017

(87) PCT Pub. No.: WO2016/108654
PCT Pub. Date: Jul. 7, 2016

(65) Prior Publication Data
US 2017/0362293 A1 Dec. 21, 2017

(30) Foreign Application Priority Data
Dec. 31, 2014 (KR) .................. 10-2014-0195793

(51) Int. Cl.
| | |
|---|---|
| *C07K 14/605* | (2006.01) |
| *A61K 38/26* | (2006.01) |
| *C07K 16/00* | (2006.01) |
| *C07K 19/00* | (2006.01) |
| *A61P 1/00* | (2006.01) |
| *A61P 1/12* | (2006.01) |
| *A61P 3/08* | (2006.01) |
| *A61P 3/10* | (2006.01) |
| *A61K 39/00* | (2006.01) |

(52) U.S. Cl.
CPC .......... *C07K 14/605* (2013.01); *A61K 38/26* (2013.01); *A61P 1/00* (2018.01); *A61P 1/12* (2018.01); *A61P 3/08* (2018.01); *A61P 3/10* (2018.01); *C07K 16/00* (2013.01); *C07K 19/00* (2013.01); *A61K 2039/505* (2013.01); *C07K 2317/52* (2013.01); *C07K 2317/53* (2013.01); *C07K 2317/76* (2013.01); *C07K 2317/94* (2013.01); *C07K 2319/30* (2013.01)

(58) Field of Classification Search
CPC ... C07K 14/605; C07K 16/00; C07K 2317/30
See application file for complete search history.

(56) References Cited

U.S. PATENT DOCUMENTS

| | | | |
|---|---|---|---|
| 6,006,753 A | 12/1999 | Efendic | |
| 6,747,006 B2 * | 6/2004 | Efendic | .................. A61K 38/26 514/11.7 |
| 7,452,966 B2 | 11/2008 | Glaesner et al. | |
| 7,867,491 B2 | 1/2011 | Yang et al. | |
| 8,278,420 B2 * | 10/2012 | Wang | .................. A61K 39/0008 530/387.1 |
| 8,586,038 B2 | 11/2013 | Yang et al. | |
| 2008/0300188 A1 * | 12/2008 | Yang | ...................... C12N 15/62 514/7.6 |
| 2011/0091416 A1 | 4/2011 | Yang et al. | |
| 2012/0189627 A1 | 7/2012 | Heavner | |
| 2014/0377290 A1 | 12/2014 | Kim et al. | |

FOREIGN PATENT DOCUMENTS

| | | |
|---|---|---|
| KR | 10-2014-0037961 A | 3/2014 |
| WO | 98/08531 A1 | 3/1998 |
| WO | 98/19698 A1 | 5/1998 |
| WO | 99/64060 A1 | 12/1999 |
| WO | 00/07617 A1 | 2/2000 |
| WO | 00/16797 A2 | 3/2000 |
| WO | 2008/147143 A2 | 12/2008 |

OTHER PUBLICATIONS

Wolfgang Glaesner, et al., "Engineering and characterization of the long-acting glucagon-like peptide-1 analogue LY2189265, an Fc fusion protein", Diabetes/Metabolism Research and Reviews, 2010, pp. 287-296, vol. 26.
Dong-Myung Kim, et al., "Fc fusion to Glucagon-like peptide-1 inhibits degradation by human DPP-IV, increasing its half-life in serum and inducing a potent activity for human GLP-1 receptor activation", BMB reports, 2009, pp. 212-216, vol. 42, Issue No. 4.
International Searching Authority, International Search Report of PCT/KR2015/014542, dated May 4, 2016. [PCT/ISA/210].
Extended European Search Report dated May 17, 2018 for related European Patent Application No. 15875748.4.
Se Jin Im et al: "Natural Form of Noncytolytic Flexible Human Fc as a Long-Acting carrier of Agonistic Ligand, Erythropoietin", PLOS ONE, vol. 6, No. 9, Sep. 16, 2011 (Sep. 16, 2011), p. e24574, XPO55468250, DOI: 10.1371/journal.pone.0024574.

\* cited by examiner

*Primary Examiner* — Gyan Chandra
(74) *Attorney, Agent, or Firm* — Sughrue Mion, PLLC

(57) ABSTRACT

The present invention relates to a fusion polypeptide containing a glucagon-like peptide (GLP) and an immunoglobulin hybrid Fc, and more specifically, to a fusion polypeptide with an increased half-life and improved efficacy compared to the conventional fusion polypeptide based on the discovery of an immunoglobulin hybrid Fc suitable for GLP or analogs thereof, and a pharmaceutical composition for treating diabetes, inflammatory bowel disease, endoenteritis or diarrhea caused by anticancer chemotherapy, or short bowel syndrome, containing the fusion polypeptide. The fusion polypeptide of the present invention has an increased half-life and improved resistance to DPP-4 enzyme compared to those of GLP-1 and GLP-2, and it thus has improved drug efficacy in treating diabetes, inflammatory bowel disease, endoenteritis or diarrhea caused by anticancer chemotherapy, or short bowel syndrome, compared to those of the conventional drugs. Accordingly, the fusion polypeptide of the present invention can be effectively applied to pharmaceutical drugs.

12 Claims, 14 Drawing Sheets
Specification includes a Sequence Listing.

[FIG. 3]
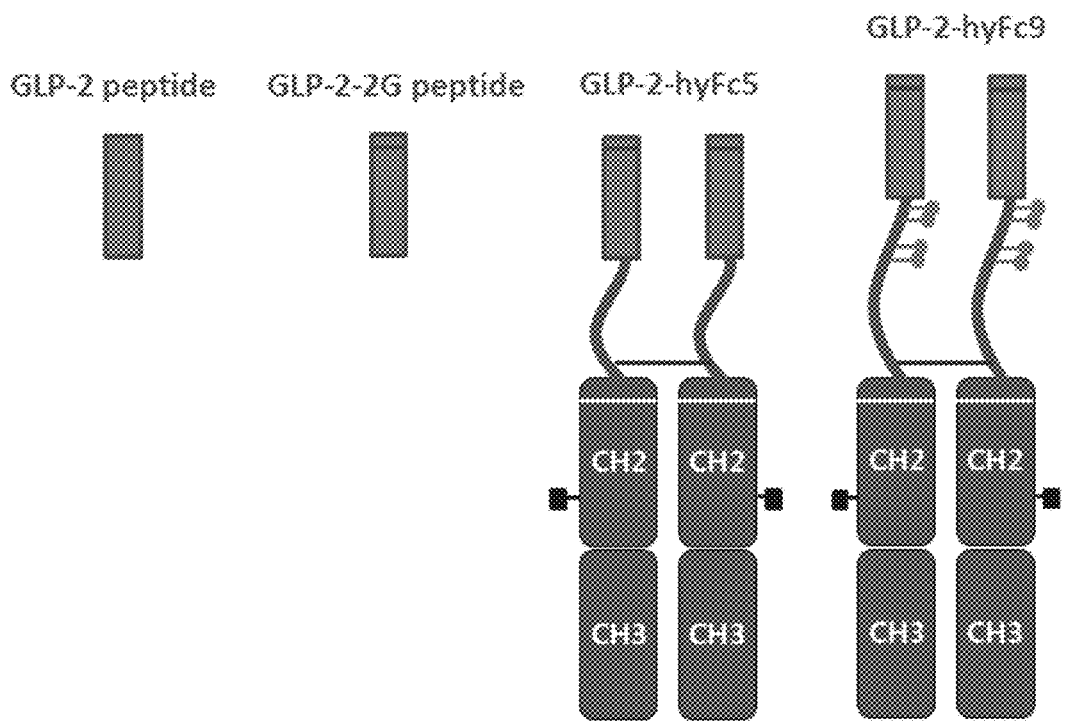
[FIG. 4]
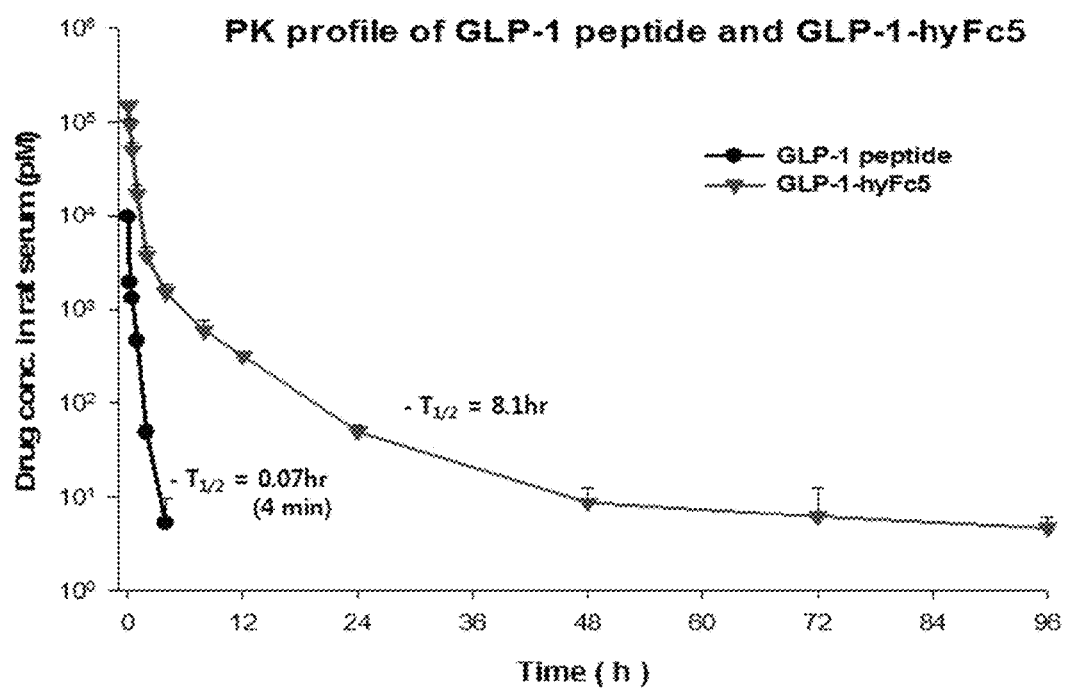

[FIG. 5]
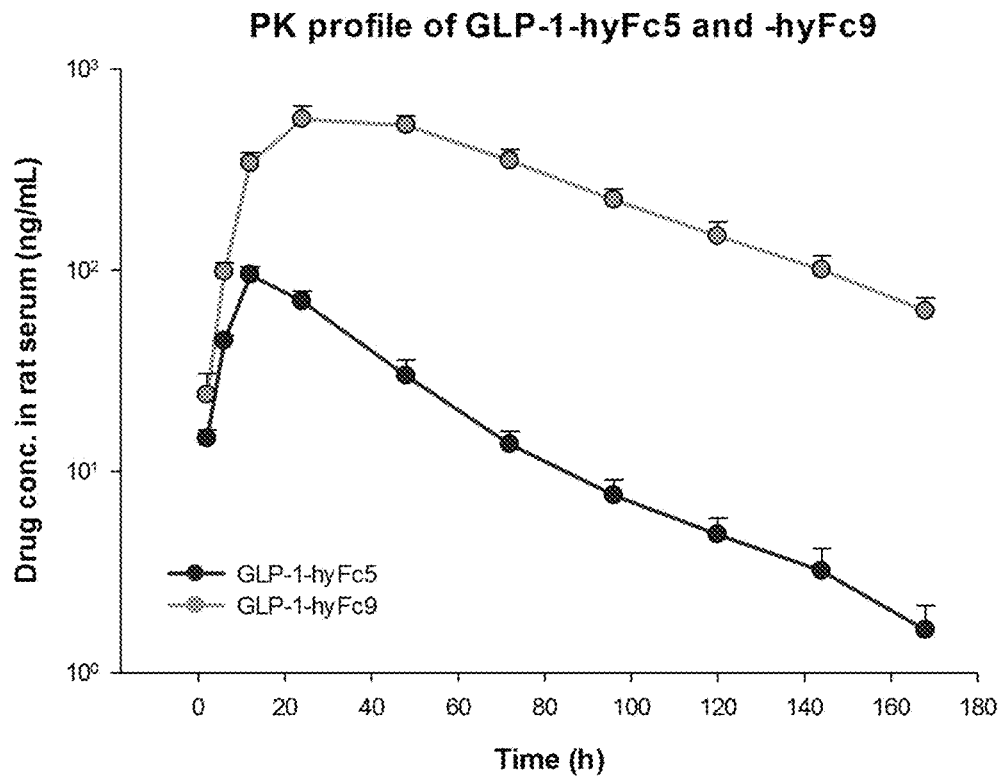
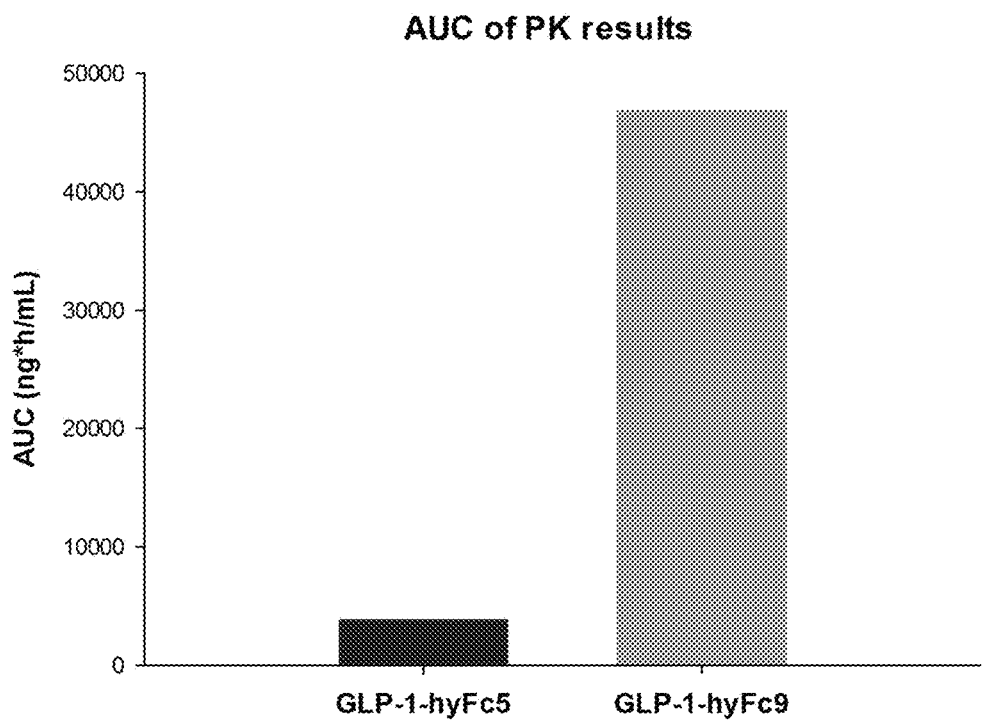

[FIG. 6]
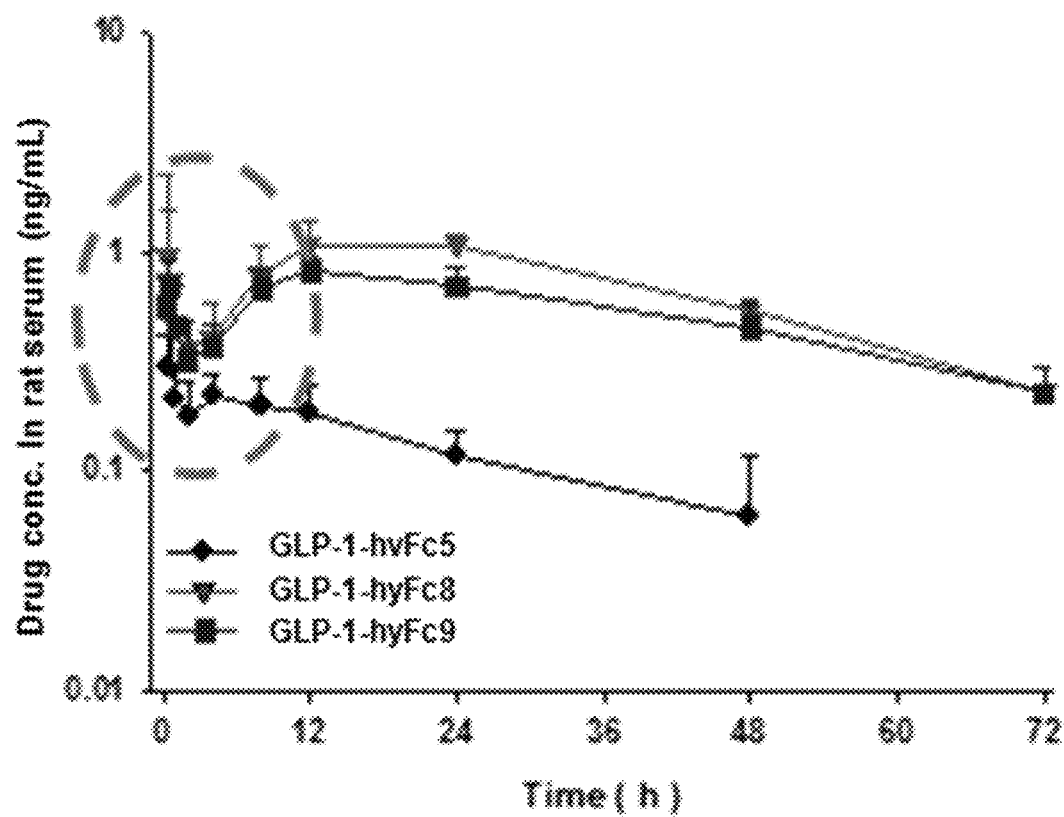

[FIG. 7]
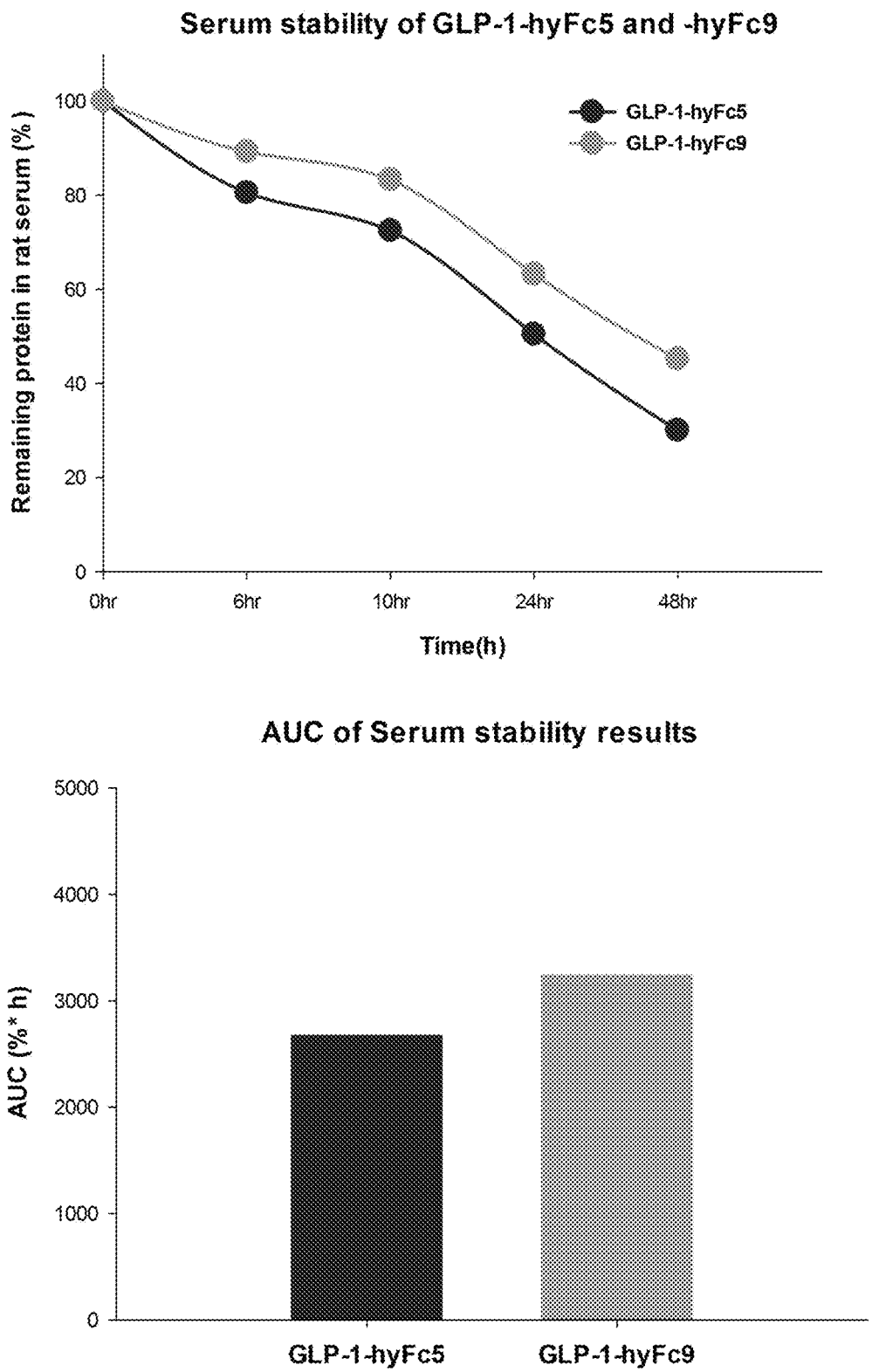

[FIG. 8]
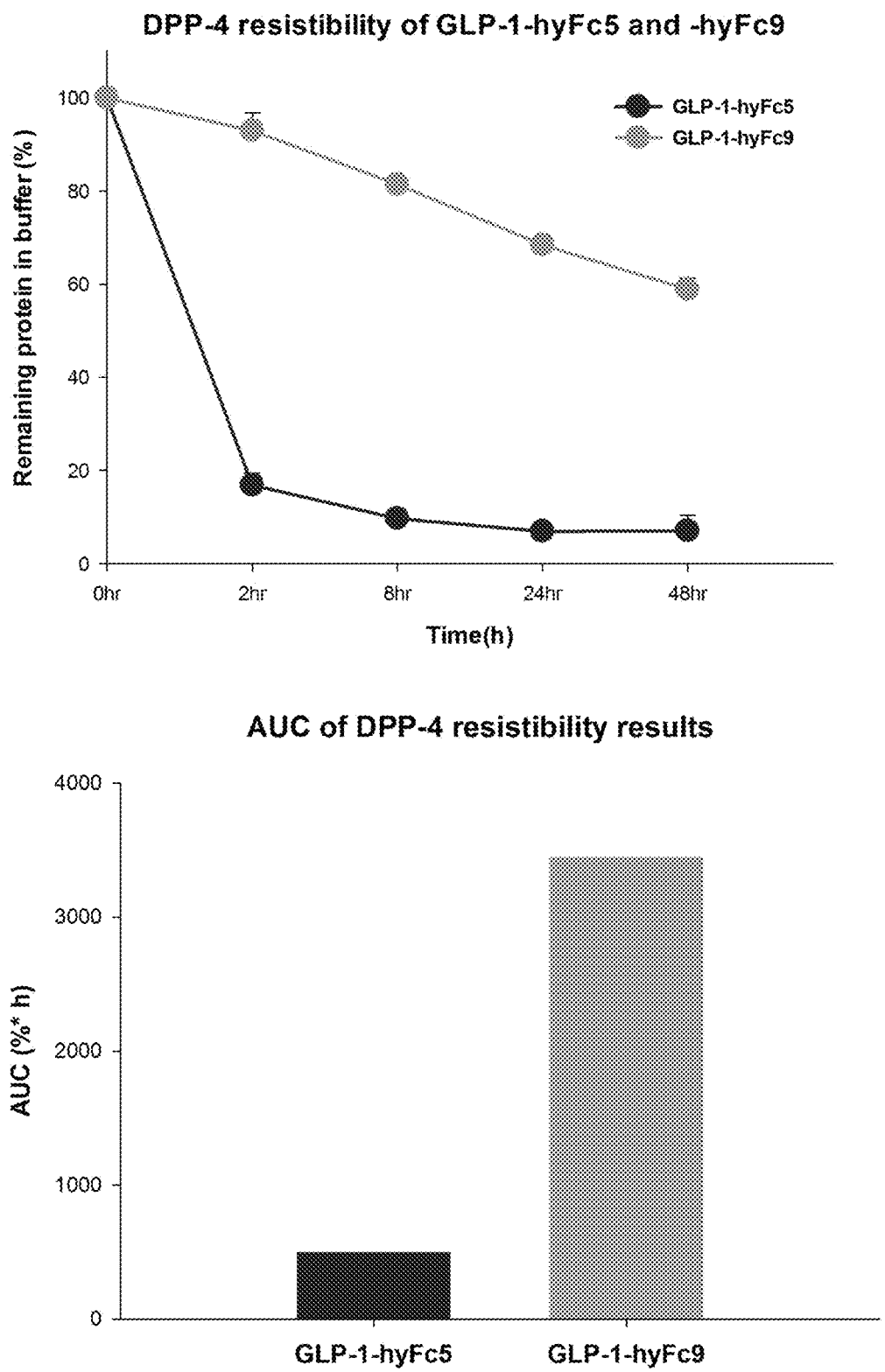

[FIG. 9]
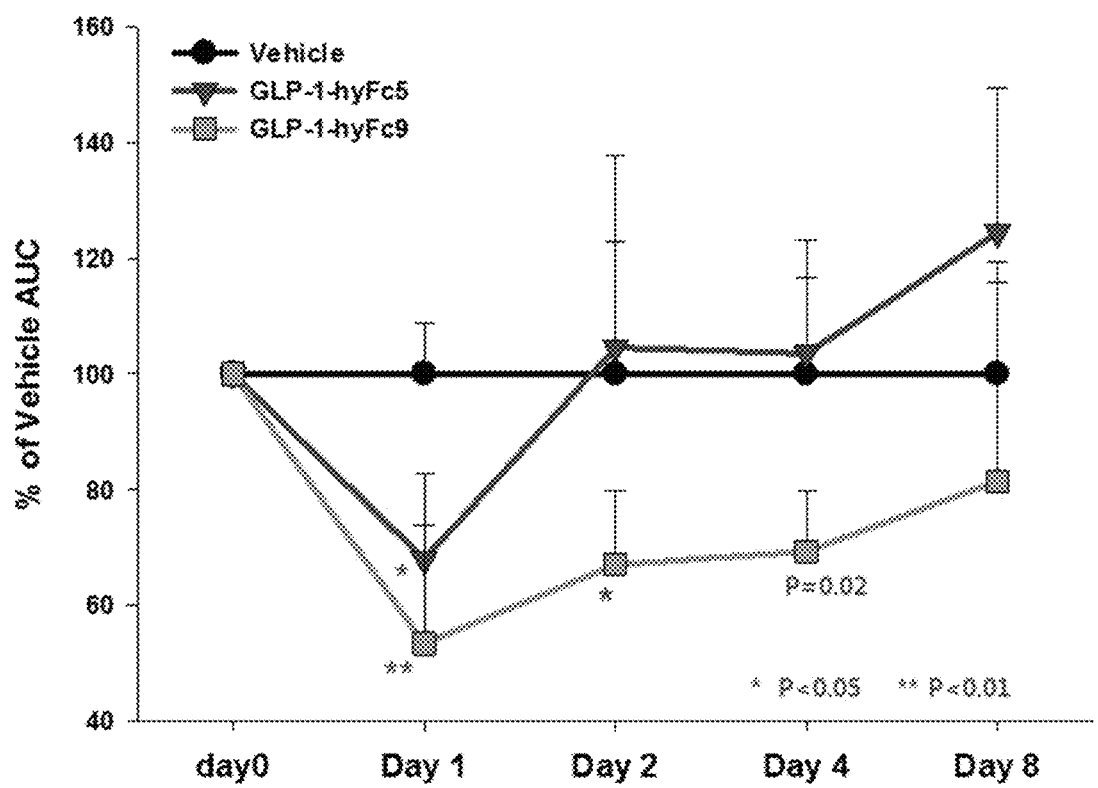

[FIG. 10]
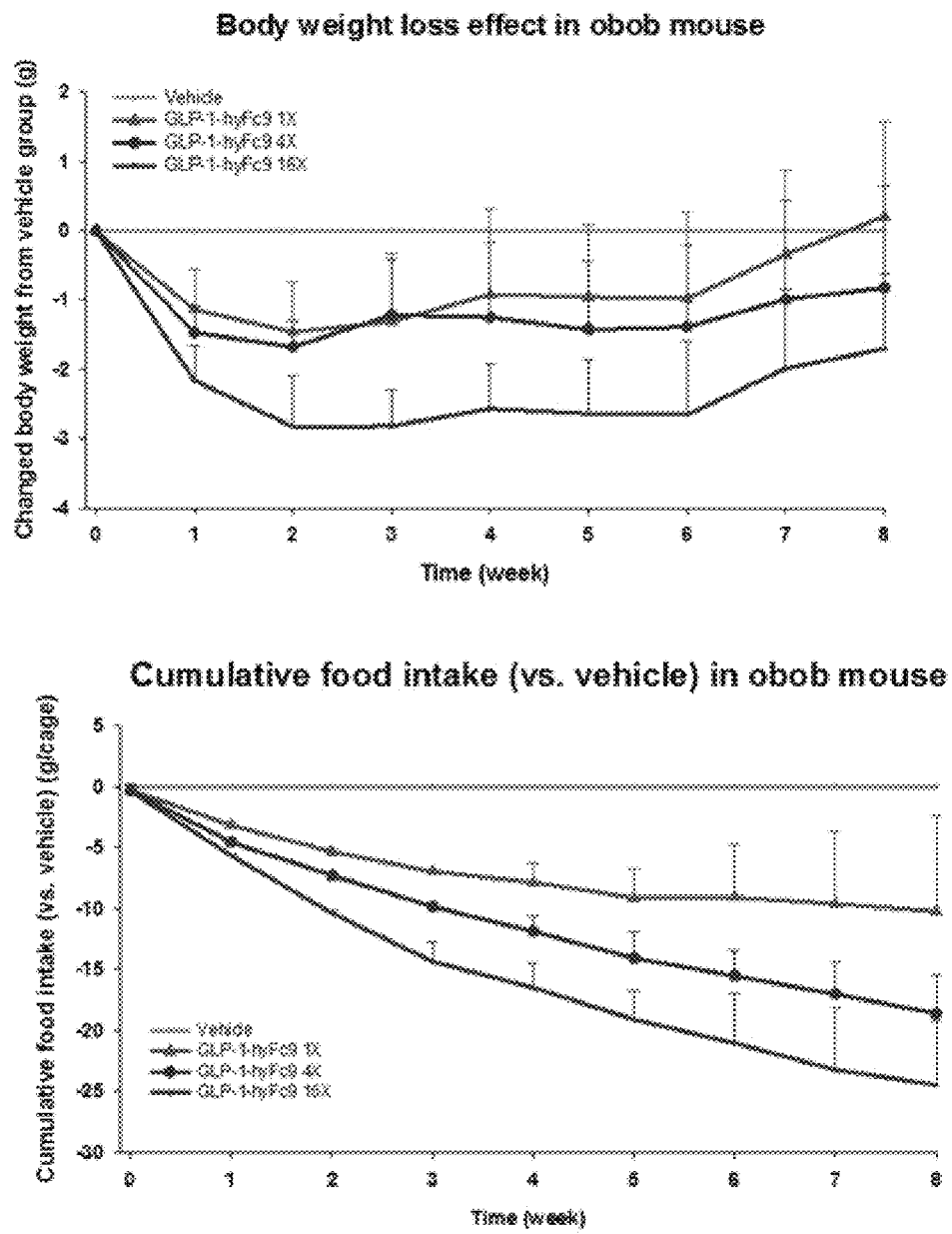

[FIG. 11]
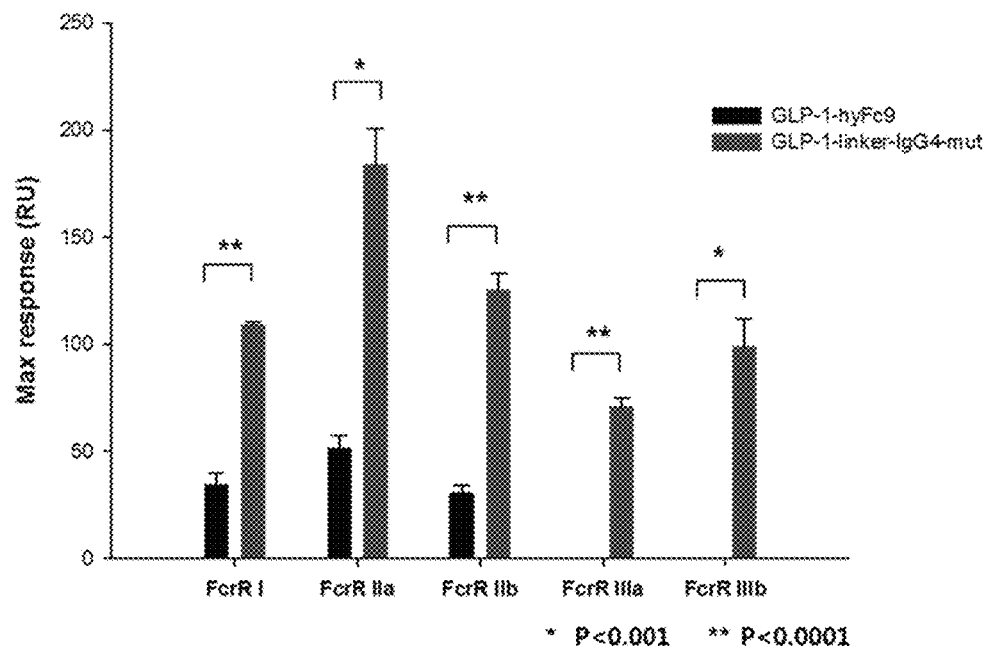
[FIG. 12]
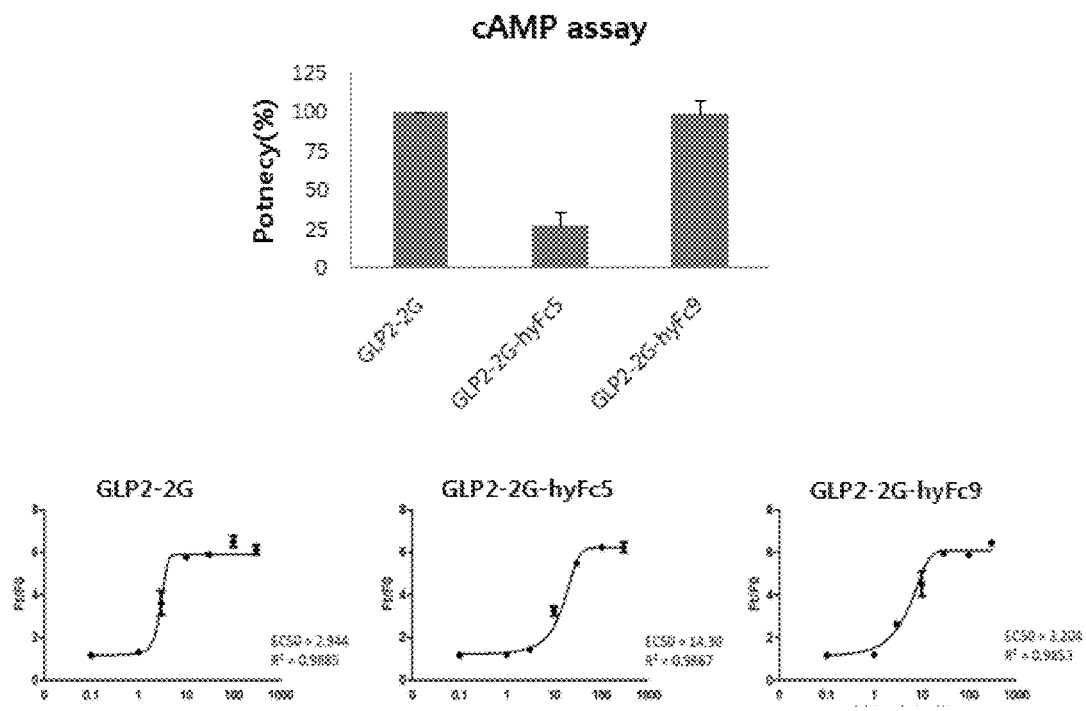

[FIG. 13]
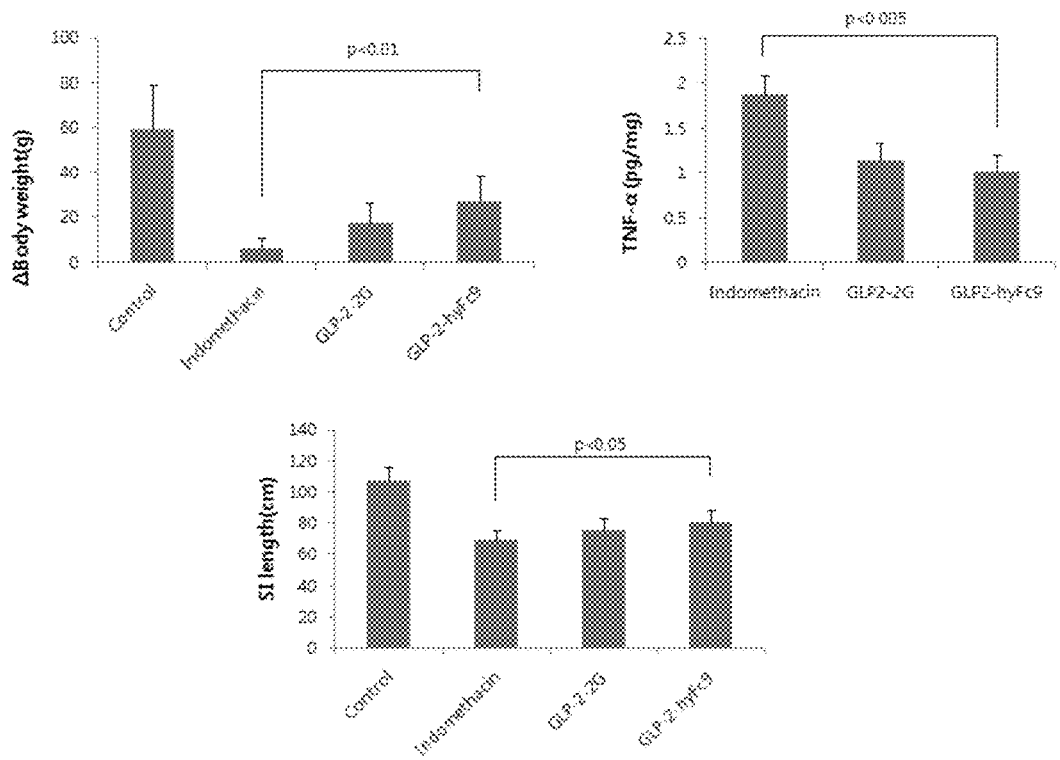
[FIG. 14]
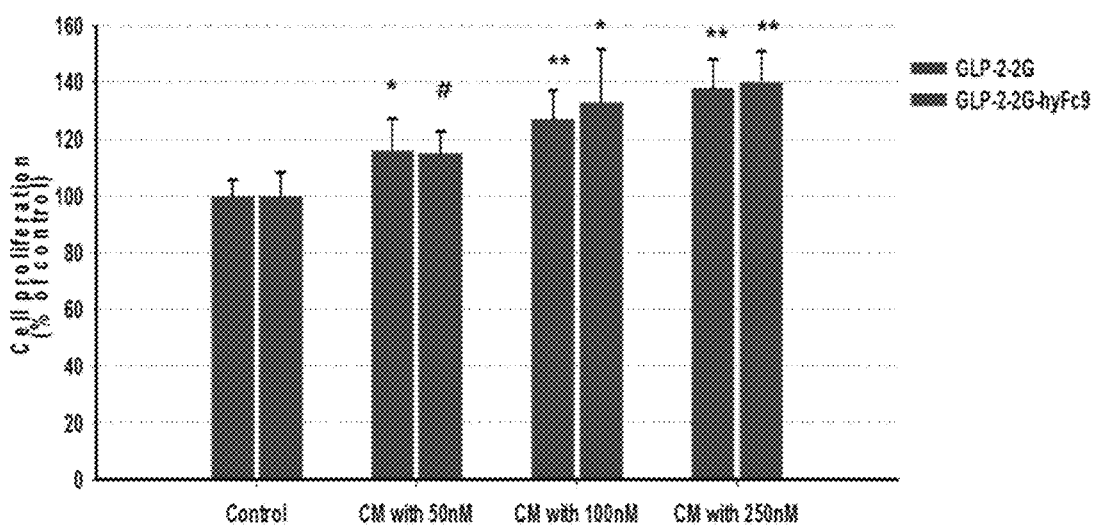

[FIG. 15]
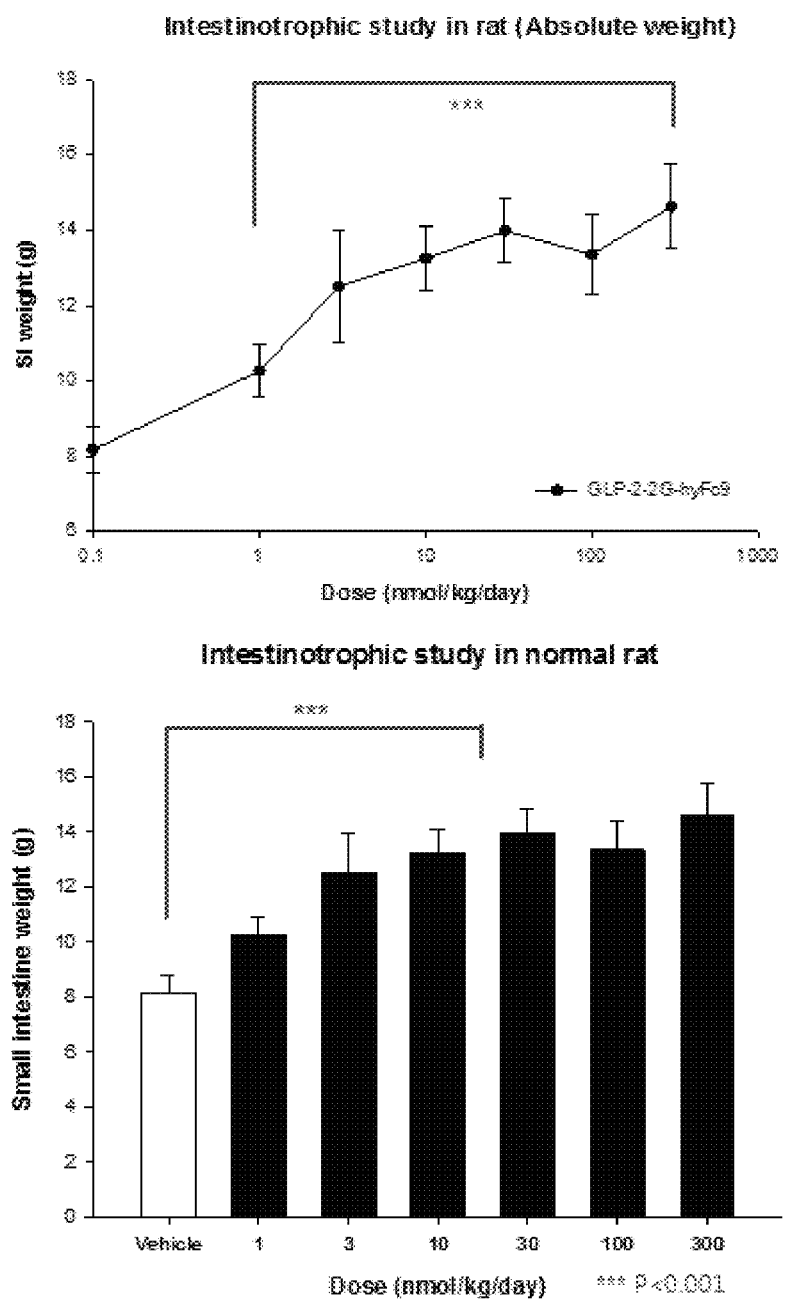

[FIG. 16]
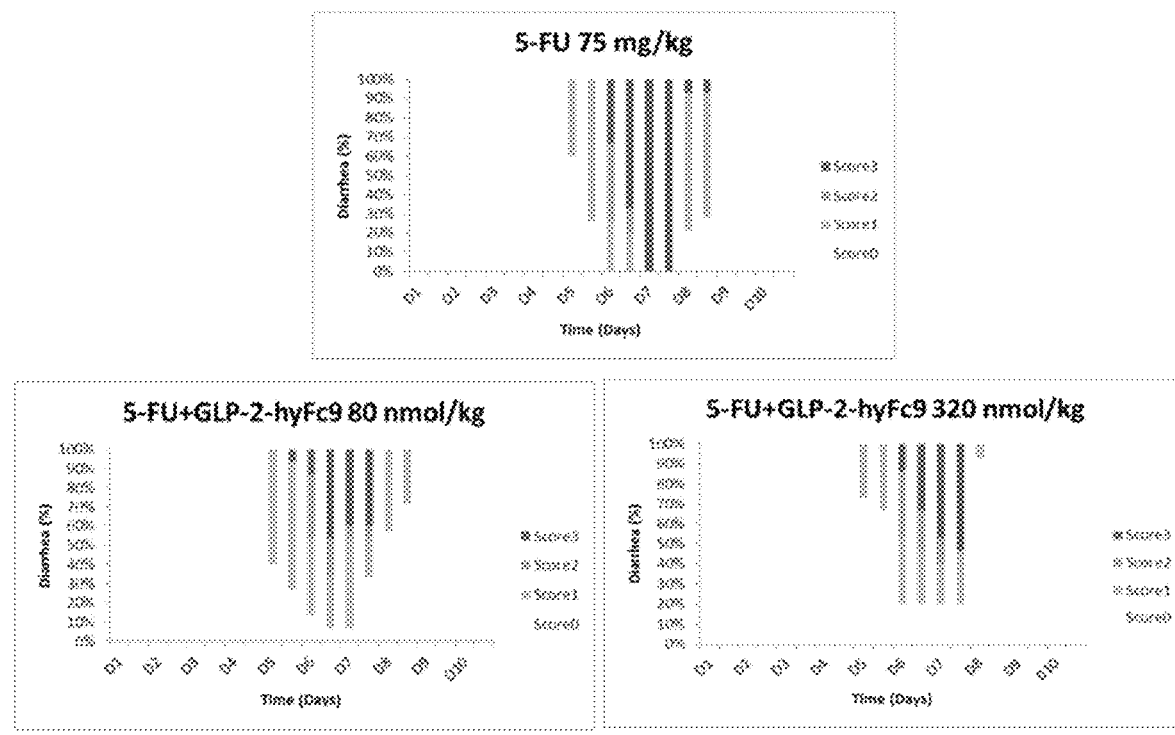

[FIG. 17]
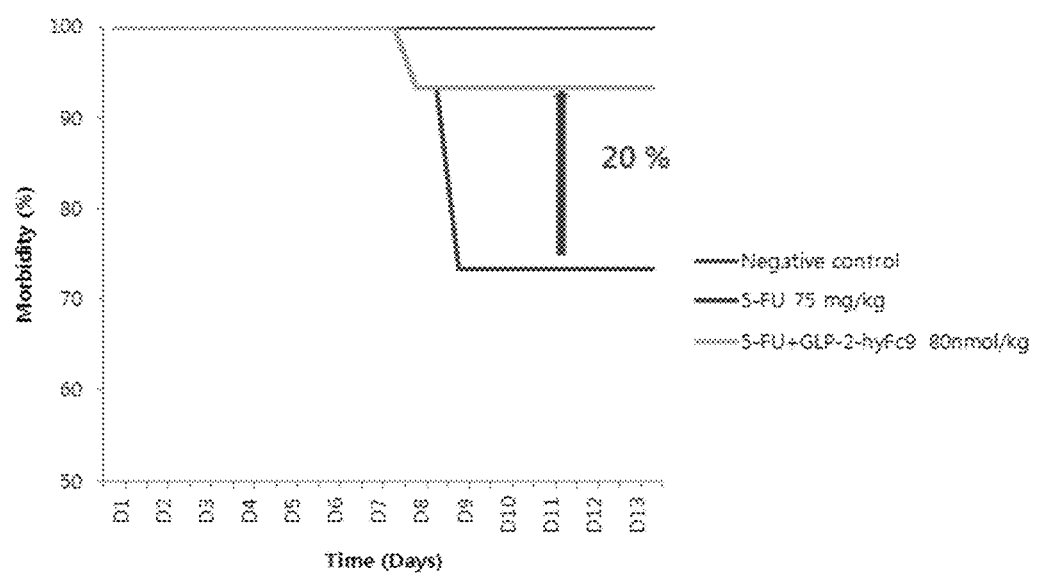

FUSION POLYPEPTIDE CONTAINING GLP AND IMMUNOGLOBULIN HYBRID FC AND USE THEREOF

CROSS REFERENCE TO RELATED APPLICATIONS

This application is a National Stage of International Application No. PCT/KR2015/014542 filed Dec. 31, 2015, claiming priority based on Korean Patent Application No. 10-2014-0195793, filed Dec. 31, 2014, the contents of all of which are incorporated herein by reference in their entirety.

TECHNICAL FIELD

The present invention relates to a fusion polypeptide containing a glucagon-like peptide (GLP) and an immunoglobulin hybrid Fc, and more specifically, to a fusion polypeptide with an increased half-life and improved efficacy compared to the conventional fusion polypeptide based on the discovery of an immunoglobulin hybrid Fc suitable for GLP or analogs thereof, and a pharmaceutical composition for treating diabetes, inflammatory bowel disease, endoenteritis or diarrhea caused by anticancer chemotherapy, or short bowel syndrome, containing the fusion polypeptide. Additionally, a polynucleotide encoding the fusion polypeptide, an expression vector containing the polynucleotide, and a host cell containing the expression vector are also included in the scope of the present invention.

BACKGROUND ART

Diabetes is a metabolic disease, which causes a problem in insulin secretion or insulin function due to genetic or environmental reasons and thus the glucose in the blood cannot be utilized as an energy source for cells, thereby showing the symptoms of hyperglycemia having high blood glucose levels. Diabetes can cause complications and is one of the most serious chronic diseases in modern society.

Diabetes can be largely classified into type 1 diabetes and type 2 diabetes. Type 1 diabetes accounts for less than 10% of the total diabetic patients and mostly occurs in children. Reportedly, type 1 diabetes occurs when the pancreatic β cells fail to produce or secrete insulin by their destruction due to auto-immune diseases, etc., and thus type 1 diabetic patients require lifetime insulin injections. In contrast, type 2 diabetes accounts for 90% or more of the total diabetic patients and mostly occurs in adults, and in particular, more frequently in overweight and obese adults. Reportedly, type 2 diabetes is caused by defective insulin secretion or insulin resistance in the pancreas.

For the treatment of diabetes, people usually start with physical exercise and diet therapy. However, when these efforts fail to control the blood glucose levels, a single or combined diabetic agent may be administered. According to the American Diabetes Association (ADA) guidelines, the first-selection drug is metformin, the second- and third-selection drugs include sulfonylurea-based, glinide-based, thiazolidinedione-based, DPP-4 inhibitors, etc., and injections, such as a glucagon like peptide-1 (GLP-1) agonist, or insulin injections are followed thereafter.

The conventional oral therapeutic agents currently used in clinical treatment have the advantage of capable of continuously maintaining normal blood glucose levels, however, the long-term administration of these agents not only causes various adverse effects such as causing hypoglycemia, diarrhea, body weight gain, cardiovascular problems, hepatotoxicity, etc., but also causes destruction of the pancreatic β cells, thereby ultimately requiring an insulin injection. Additionally, the insulin injection, as the final treatment, must be administered subcutaneously two to three times daily thus causing inconveniences, and the insulin injection may possibly induce hypoglycemia, which is one of the most serious adverse effects.

While making efforts to remedy these problems, GLP-1 has been on the spotlight recently as the next generation diabetes treatment. GLP-1 and analogs and derivatives thereof have shown good potentials as therapeutic agents for treating type 2 diabetes in clinical trials. They can induce numerous biological effects, such as stimulating insulin secretion, inhibition of glucagon secretion, inhibition of gastric emptying, inhibition of gastric- or intestinal motility, induction of reducing body weight, etc. Additionally, they can protect the pancreas during a long-term administration, are free of hypoglycemia, and maintain appropriate blood glucose levels for a long period of time.

However, GLP-1 is degraded by DPP-4 in-vivo and becomes inactive thereby having a very short half-life in-vivo, which makes it difficult to be developed as a therapeutic agent. Accordingly, various approach methods have been conducted in order to prolong the half-life of GLP-1 or reduce the peptide removal rate from the body while maintaining its biological activities. That is, various GLP-1 analogs have been actively developed, and an approach method to fuse GLP-1 to an immunoglobulin Fc region has been attempted (U.S. Pat. No. 7,452,966 B2, etc.).

Nevertheless, the application of the technology to fuse immunoglobulin Fc has not progressed sufficiently for its commercialization, from the aspect of limitations in half-life, antibody-dependent cell cytotoxicity (ADCC)-inducing capacity, stability for DPP-4 enzyme, etc.

Meanwhile, inflammatory bowel disease (IBD) is thought to occur due to genetic and immunological factors, however, it is an incurable disease in which the causes and treatments still remain to be elucidated. It is a chronic disease caused by the inflammation on the inner wall of the digestive tract, and inflammatory bowel diseases are largely classified into ulcerative colitis and Crohn's disease.

Ulcerative colitis (UC) is a chronic inflammatory disease which occurs on the mucous membrane of the large intestine of the digestive tract, and the inflammation begins from the rectum and is continuously connected to the large intestine. Patients with ulcerative colitis commonly complain of diarrhea, bloody stool, abdominal pain, etc., and symptoms such as anorexia, weight loss, fatigue, etc., are often accompanied as well. In most cases, ulcerative colitis is an intermittent disease repeatedly featuring the periods of exacerbated symptoms and those of ameliorated symptoms, and sometimes there are also long periods that are symptom-free.

In Crohn's disease (CD), unlike ulcerative colitis, inflammation invades the entire layers of the intestine and the distribution of lesions is not continuous but is rather scattered around in many cases. The frequently occurring symptoms of Crohn's disease include diarrhea, abdominal pain, anorexia, etc., but the kinds and degrees of the symptoms vary greatly depending on the patients. In fact, the patients with Crohn's disease appear to experience more severe pain compared to those with ulcerative colitis, and the long-term progress and responses to treatments of the patients with Crohn's disease are much worse, thus often making them undergo surgery.

Although the effective treatment leading to a complete cure of inflammatory bowel disease is still not known because the causes of the inflammatory bowel disease have not been identified yet, studies on the factors affecting the progress of the inflammatory bowel disease have been considerably advanced, and various drugs for reducing inflammation have been developed and are currently in use. The therapeutic agents for inflammatory bowel disease widely used at present are applied sequentially in the order of anti-inflammatory agents (5-aminosalicylic acid; 5-ASA), steroidal agents, immunosuppressive agents such as 6-mercaptopyrine (6-MP), and biological agents such as TNFα inhibitors (anti-TNFα antibody, Infliximab), according to the severity of symptoms. However, these agents currently in use have shown various adverse effects, and accordingly, there is an urgent need for the development of 1) a biological agent having the efficacy to compensate or replace that of the existing drugs, or 2) a biological agent employing a mechanism different from that of the existing drugs.

In an effort to compensate these problems, GLP-2 has been on the spotlight recently as a therapeutic agent for inflammatory bowel disease. GLP-2, which is secreted from the L cells in the intestine, induces the production of IGF-1, nitric oxide (NO), vasoactive intestinal peptide (VIP), etc., through the signaling of GLP-2 receptors expressed in the intestinal cells. The thus-produced IGF-1 induces the growth of the intestinal cells through the signaling of PI-3K and AKT, and NO helps to improve the blood circulation in the intestine. Additionally, since GLP-2 is known to have the anti-inflammatory effect by inducing VIP production, it is also being experimentally confirmed in various research groups that GLP-2 is effective for the treatment of short bowel syndrome as well as for inflammatory bowel disease.

In fact, Gattex® (teduglutide), a GLP-2 analog, was developed by NPS pharmaceuticals, Inc. (USA) at the end of 2012, approved as an orphan drug for the treatment of short bowel syndrome (SBS), and after expanding indications, it is currently in clinical phase 2 studies among patients with inflammatory bowel disease.

However, although Gattex® has a significantly increased half-life compared to that of native GLP-2, it should be also injected once daily, thus still not satisfying unmet needs from the aspect of patient convenience. Furthermore, when the drug is to be applied to inflammatory bowel disease, which is an autoimmune disease requiring lifetime treatment, it should be developed in the form of a long-acting therapeutic agent that can be administered from at least once a week to once a month. That is, since GLP-2 is a peptide hormone, it has a significantly decreased duration compared to that of protein drugs, and thus there is a need for a method of improving the long-term duration of GLP-2.

On the other hand, since cancer cells are characterized by having rapid growth and division, most anticancer agents are designed to kill rapidly growing cells. However, some normal cells also grow rapidly like cancer cells and thus these normal cells are also damaged by anticancer chemotherapy. The rapidly growing and dividing cells among normal cells, i.e., blood cells formed in bone marrow, epithelial cells in the gastrointestinal tract containing oral cavity, hair cells, and germ cells, which produce sperms and ova, are affected more seriously. In particular, anticancer agents frequently cause mucositis in the gastrointestinal tract which may cause diarrhea, and in the case of serious diarrhea, ringer's solution and nutrients should be supplied via intravenous injection to prevent dehydration. In such a case, the preset anticancer chemotherapy schedule may have to be changed thus considerably affecting on cancer treatment. Accordingly, it is considered essential to prevent endoenteritis or diarrhea caused by anticancer chemotherapy in advance because it can reduce the pain of patients while maximizing anticancer effect. In the case of GLP-2, it can induce the proliferation of crypt cells, which form the villi of the small intestine, thereby capable of rapidly recovering from adverse effects due to anticancer chemotherapy, and the development of a GLP-2 analog with a long-term duration can prevent endoenteritis or diarrhea caused by anticancer chemotherapy in advance, by means of one injection for each cycle.

Under these circumstances, the present inventors, in order to develop a long-acting therapeutic agent by increasing the in-vivo half-lives of short-length peptides containing GLP, such as GLP-1 and GLP-2, employed the immunoglobulin hybrid Fc technology disclosed in International Publication No. WO 2008-147143, which was filed previously by the present inventors, selected the immunoglobulin Fc optimized to be specific to glucagon-like peptide (GLP), and prepared a fusion polypeptide with excellent resistance to DPP-4 enzyme while having an increased half-life, thereby completing the present invention.

DISCLOSURE

Technical Problem

An object of the present invention is to provide a fusion polypeptide including (a) glucagon-like peptide (GLP) or an analog thereof; and (b) an immunoglobulin Fc polypeptide containing a limited number of IgD hinge region.

Another object of the present invention is to provide a pharmaceutical composition for treating diabetes, inflammatory bowel disease, endoenteritis or diarrhea caused by anticancer chemotherapy, or short bowel syndrome, containing the fusion polypeptide as an active ingredient.

Still another object of the present invention is to provide a polynucleotide encoding the fusion polypeptide, an expression vector including the polynucleotide, and a host cell including the expression vector.

Technical Solution

In order to achieve the above objects, in an aspect, the present invention provides a fusion polypeptide including (a) GLP or an analog thereof; and (b) an immunoglobulin Fc polypeptide containing a limited number of IgD hinge regions.

Specifically, the fusion polypeptide may include (a) glucagon-like peptide (GLP) or an analog thereof, and (b) an immunoglobulin Fc polypeptide, in which the immunoglobulin Fc polypeptide includes (i) an isolated IgD hinge region consisting of an amino acid sequence of 35 to 49 consecutive amino acid residues from the C-terminus of SEQ ID NO: 25; and (ii) a CH2 domain and a CH3 domain consisting of an amino acid sequence of SEQ ID NO: 29.

Preferably, the C-terminus of the GLP or an analog thereof may be conjugated to the N-terminus of the immunoglobulin Fc polypeptide, and within the immunoglobulin Fc polypeptide, the C-terminus of the IgD hinge region may be conjugated to the N-terminus of the CH2 domain and the CH3 domain. Accordingly, the GLP or an analog thereof; the IgD hinge region; and the CH2 domain and the CH3 domain may be sequentially conjugated from the N-terminus to the direction of the C-terminus. As used herein, the term "fusion polypeptide" refers to a form in which a biologically active molecule, such as GLP, and the immunoglobulin Fc polypeptide are fused together, and may be used interchangeably with terms such as "Fc fusion polypeptide" and "fusion protein".

In the present invention, the glucagon-like peptide (GLP) is a concept encompassing both GLP-1 and GLP-2.

Although GLP-1 and GLP-2 peptides differ from each other in terms of in-vivo action mechanism and functions, they, being peptides produced from a single mRNA precursor of the proglucagon gene, have a high amino acid sequence homology, have the same cleavage site for DPP-4 enzyme, and are hormones having similar molecular characteristics. Therefore, when the glucagon-like peptide (GLP) containing GLP-1 or GLP-2 is conjugated to the immunoglobulin Fc polypeptide, a similar form may be applied. Specifically, when the GLP is conjugated to the hybrid Fc (hyFc) polypeptide developed by the present inventors, a similar form of hyFc may be applied thereto.

As used herein, the term "GLP-1 (glucagon-like peptide-1)" is a type of incretins, which are hormones secreted in the digestive tract. In fact, GLP-1 is a protein secreted from intestinal L-cells in a diet-dependent manner known to play the role of increasing pancreatic insulin secretion and the role of inhibiting the increase of blood glucose levels after a meal by inhibiting the secretion of glucagon. As such, the therapeutic use of GLP-1 for treating diabetes has already been widely known, and there is also a report that GLP-1 is involved in the physiological control of appetite thus having an effect of reducing body weight.

On the other hand, the native GLP-1 is processed in-vivo so that the initial six amino acids can be cleaved from the molecule. According to the customary practice in the art to which the present invention pertains, the N-terminus of GLP-1 is designated as No. 7 while the C-terminus of GLP-1 is designated as No. 37. According to the process, GLP-1 may be processed from the GLP-1 (1-37), a form without the function of insulin secretion, into a form of the GLP-1 (7-37) (the amino acid sequence of SEQ ID NO: 1 and the nucleic acid sequence of SEQ ID NO: 33) to be an active form, and may be further modified in-vivo so that the glycine residue at the C-terminus can be removed and replaced with an amide group, thereby becoming GLP-1 (7-36) amide (the amino acid sequence of SEQ ID NO: 3 and the nucleic acid sequence of SEQ ID NO: 35). Accordingly, GLP-1(7-37) OH and GLP-1(7-36) amide correspond to two native types of GLP-1.

However, native GLP-1 has many limitations to be developed as a drug because, for example, it is very rapidly cleaved in-vivo by DPP-4 enzyme and becomes inactive, and thus there have been many attempts to increase its in-vivo half-life. In this regard, attempts have been made to prepare GLP-1 analogs by causing a modification in GLP-1 thereby reducing the cleavage by DPP-4 enzyme, and to this end, GLP-1 analogs known in the art may be used without limitation.

Specifically, the substitution of the amino acid at position 8 can reduce the rate that DPP-4 enzyme inactivates GLP-1; the substitution of the amino acid at position 22 can reduce the possibility of adhesion of molecules and increase the efficacies of molecules; and the substitution of the amino acid at position 36 can reduce the risk that a fusion protein may induce a neutralizing immune response after repeated and continuous administration. Accordingly, GLP-1 analogs having an amino acid substitution at position 8, 22, or 36, respectively, may be used, although not limited thereto. Additionally, as disclosed in U.S. Pat. No. 7,452,966 B2, etc., analogs which have an amino acid substitution at position 33, 34, or 37, respectively, may be used.

In a more specific embodiment, the GLP-1 analogs may be preferably those which has a modification on the region cleaved by DPP-4 enzyme. DPP-4 enzyme cleaves GLP-1 in between amino acids at positions 8 and 9, and thus, the GLP-1 analogs in which alanine (A), the amino acid at position 8, is substituted with glycine (G) or valine (V), can reduce the cleavage by DPP-4 enzyme.

Additionally, the GLP-1 analogs may be those in which glycine (G), the amino acid at position 22, is substituted with glutamic acid (E); or arginine (R), the amino acid at position 36, is substituted with glycine (G).

Accordingly, preferably, the GLP-1 analogs may be those having the amino acid sequence of SEQ ID NO: 2, 3, 4, 5, 6, 7, 8, 9, 10, 11, or 12, in which the amino acids at position 8, 22, and/or 36 of GLP-1 (7-37) are substituted; or may be those having the amino acid sequence of SEQ ID NO: 14, 15, 16, 17, 18, 19, 20, 21, 22, 23, or 24, in which the amino acids at position 8, 22, and/or 36 of GLP-1 (7-36) are substituted. Additionally, more preferably, the GLP-1 analogs may be those having the amino acid sequence of SEQ ID NO: 2, 3, 6, 7, 8, 9, 11, 12, 14, 15, 18, 19, 20, 21, 23, or 24, in which the amino acid at position 8, the cleavage site by DPP-4 enzyme, is modified, and most preferably, a GLP-1 analog having the amino acid sequence of SEQ ID NO: 2, in which alanine (A), the amino acid at position 8, is substituted with glycine (G). The GLP-1 analog having the amino acid sequence of SEQ ID NO: 2 may be encoded by the nucleic acid sequence of SEQ ID NO: 34. In an exemplary embodiment of the present invention, the efficacy was confirmed using the GLP-1 analog which has the amino acid sequence of SEQ ID NO: 2. The positions of modifications in the GLP-1 analogs are summarized in Table 1 below.

TABLE 1

| GLP-1 (7-37) | | GLP-1 (7-36) | |
| --- | --- | --- | --- |
| SEQ ID NO | Position of modification | SEQ ID NO | Position of modification |
| 2 | A8G | 14 | A8G |
| 3 | A8V | 15 | A8V |
| 4 | G22E | 16 | G22E |
| 5 | R36G | 17 | R36G |
| 6 | A8G G22E | 18 | A8G G22E |
| 7 | A8V G22E | 19 | A8V G22E |
| 8 | A8G R36G | 20 | A8G R36G |
| 9 | A8V R36G | 21 | A8V R36G |
| 10 | G22E R36G | 22 | G22E R36G |
| 11 | A8G G22E R36G | 23 | A8G G22E R36G |
| 12 | A8V G22E R36G | 24 | A8V G22E R36G |

As used herein, the term "glucagon-like peptide-2 (GLP-2)" refers to a peptide hormone having 33 short amino acids (of SEQ ID NO: 44), which is generated through enzyme cleavage by an intestinal enzyme after being produced in the intestinal endocrine L cells, the secretory cells in the intestine and particular brain domains in the form of a precursor of glucagon. GLP-2 reacts to nutrient ingestion along with food intake and is co-secreted with GLP-1, oxyntomodulin, and glicentin.

GLP-2 has been widely known to be effective not only for inflammatory bowel disease but also for short bowel syndrome (SBS), etc. In fact, Gattex® (teduglutide), a GLP-2 analog, was developed by NPS pharmaceuticals, Inc. (USA) at the end of 2012, approved as an orphan drug for the treatment of short bowel syndrome (SBS), and after expanding indications, it is currently in clinical phase 2 studies among patients with inflammatory bowel disease.

GLP-2 is secreted as a 33-amino acid-peptide and can be cleaved by DPP-4 enzyme, as is the case with GLP-1. Specifically, since GLP-2 is very rapidly cleaved by DPP-4 enzyme at the amino acid at position 2, i.e., alanine (A), and thereby generates an inactive human GLP-2, it had a limitation to be developed as a drug due to the short in-vivo half-life. Accordingly, there has also been an attempt to prepare GLP-2 analogs by causing a modification in GLP-2 thereby reducing the cleavage by DPP-4 enzyme, and to this end, GLP-2 analogs known in the art may be used without limitation.

Specifically, the substitution of the amino acid at position 2 can reduce the rate that DPP-4 enzyme inactivates GLP-2. That is, GLP-2 analogs, which have an amino acid substitution at position 2 from alanine (A) to glycine (G), serine (S), or valine (V), can reduce the cleavage by DPP-4 enzyme. Additionally, in another embodiment, the GLP-2 analog disclosed in U.S. Patent Application Publication No. 2007/0117752 A1 may be used. Specifically, the substitutions may include the amino acid substitution at position 2; additional amino acid substitutions at positions 3, 5, 7, 10, and 11, and/or deletion of amino acids at positions from 31 to 33, and/or addition of a stabilizing peptide sequence at the N-terminus or C-terminus, along with amino acid substitutions at positions 8, 16, 24, and 28. More specifically, alanine (A), the amino acid at position 2, may be substituted with glycine (G), serine (S), or valine (V); aspartic acid (D), the amino acid at position 3, with glutamic acid (E); serine (S), the amino acid at position 5, with threonine (T); phenylalanine (F), the amino acid at position 6, with proline (P); serine (S), the amino acid at position 7, with threonine (T); aspartic acid (D), the amino acid at position 8, with serine (S); glutamic acid (E), the amino acid at position 9, with aspartic acid (D); methionine (M), the amino acid at position 10, with leucine (L), norleucine (Nle), or an oxidation-stable Met-substituted amino acid; asparagine (N), the amino acid at position 11, with alanine (A), lysine (K), or serine (S); threonine (T), the amino acid at position 12, with lysine (K); isoleucine (I), the amino acid at position 13, with glutamic acid (E) or glutamine (Q); leucine (L), the amino acid at position 14, with methionine (M) or norleucine (Nle); aspartic acid (D), the amino acid at position 15, with glutamic acid (E); asparagine (N), the amino acid at position 16, with alanine (A); leucine (L), the amino acid at position 17, with glutamic acid (E); alanine (A), the amino acid at position 19, with threonine (T); arginine (R), the amino acid at position 20, with lysine (K); aspartic acid (D), the amino acid at position 21, with isoleucine (I); asparagine (N), the amino acid at position 24, with alanine (A) or glutamic acid (E); glutamine (Q), the amino acid at position 28, with alanine (A) or asparagine (N); isoleucine (I), the amino acid at position 31, with proline (P) or deleted; threonine (T), the amino acid at position 32, may be deleted; and aspartic acid (D), the amino acid at position 33, may be substituted with asparagine (N) or deleted.

Various modifications described above may be applied to GLP-2, not limited thereto, and most preferably, the GLP-2 may be a GLP-2 analog having the amino acid sequence of SEQ ID NO: 45, in which alanine (A), the amino acid at position 2, is substituted with glycine (G); or a GLP-2 analog having the amino acid sequence of SEQ ID NO: 46, in which alanine (A), the amino acid at position 2, is substituted with valine (V). The GLP-2 analog having the amino acid sequence of SEQ ID NO: 45 may be encoded by the nucleic acid sequence of SEQ ID NO: 51.

Acknowledging that GLPs (GLP-1 or GLP-2) or analogs thereof cannot be appropriately used as therapeutic drugs because they are rapidly cleaved by DPP-4 enzyme and become inactive in-vivo, the present inventors, in an attempt to solve the problem, have developed an immunoglobulin Fc polypeptide suitable for GLP-1 or GLP-2 and subsequently prepared a fusion polypeptide by fusing them together. Specifically, they have attempted to significantly increase in-vivo half-life of a GLP-1 or GLP-2 thereby enabling a GLP-1 or GLP-2 to continuously exhibit drug efficacies in-vivo. Additionally, they have developed fusion polypeptides having excellence in the aspects of serum stability, DPP-4 resistance, pharmacodynamic profiles, etc.

For this purpose, the present invention aims at preparing a fusion polypeptide by fusing the hyFc5 (hFc-5), prepared in International Publication No. WO 2008/147143 according to the immunoglobulin hybrid Fc technology, to the GLP-1 or GLP-2. As used herein, the term "hybrid" refers to sequences encoding two or more immunoglobulin Fc fragments of different origins are present in a single-chain immunoglobulin Fc region. The hyFc5, which is a hyFc including an IgD hinge region with a length of 30 amino acids, showed a significant increase in half-life when applied to large proteins, but the effect was much reduced when applied to relatively short peptides, for example, to the GLP-1 or GLP-2 of the present invention, and in this regard, the fusion polypeptide with improved effect of the present invention was prepared.

As used herein, the term "immunoglobulin Fc fragment" or "immunoglobulin Fc" refers to a protein, which includes a heavy-chain constant region (CH) but not the variable regions of the heavy and light chains of an immunoglobulin and the light-chain constant region (CL). The Fc may further include a hinge region, and for the purpose of the present invention, may include the heavy-chain constant region 2 (CH2) and the heavy-chain constant region 3 (CH3), but may or may not include the heavy-chain constant region (CH1).

The immunoglobulin Fc fragment of the present invention may include the hinge region, the CH2 domain region, and the CH3 domain region, from the N-terminus to the C-terminus. Specifically, the immunoglobulin Fc fragment of the present invention may be a hybrid immunoglobulin Fc fragment. Accordingly, the hinge region may include human Ig hinge region, the CH2 domain region may include the amino acid residues of human IgD and IgG4 CH2 domains, and the CH3 domain may include the amino acid residues of human IgG4 CH3 domain.

The immunoglobulin Fc polypeptide, which is suitable for the GLP or analogs thereof of the present invention, are characterized by including an IgD hinge region with a length of 35 to 49 amino acids. The hinge region basically serves to maintain flexibility when it binds to a biological active molecule such as GLP-1 or GLP-2, thereby maintaining the structure. Specifically, the hinge region may be an isolated IgD hinge region having an amino acid sequence of 35 to 49 consecutive amino acids from the C-terminus to the N-terminus of SEQ ID NO: 25 (encoded by the nucleic acid sequence of SEQ ID NO: 36), in the amino acid sequence of SEQ ID NO: 25 of the IgD hinge region. Additionally, preferably, the hinge region may be an IgD hinge region having an amino acid sequence of 35 to 40 consecutive amino acids from the C-terminus to the N-terminus of SEQ ID NO: 25, more preferably, an IgD hinge region having an amino acid sequence of 35 to 40 consecutive amino acids, and even more preferably, an amino acid sequence of 40 consecutive amino acids. In the amino acid sequence of SEQ ID NO: 25, the IgD hinge region consisting of an amino acid sequence of 35 consecutive amino acids was indicated as SEQ ID NO: 26, the IgD hinge region consisting of an amino acid sequence of 40 consecutive amino acids as SEQ ID NO: 27, the IgD hinge region consisting of an amino acid sequence of 49 consecutive amino acids as SEQ ID NO: 28, the nucleic acid sequence encoding the amino acid sequence of SEQ ID NO: 26 as SEQ ID NO: 37, the nucleic acid sequence encoding the amino acid sequence of SEQ ID NO: 27 as SEQ ID NO: 38, and the nucleic acid sequence encoding the amino acid sequence of SEQ ID NO: 28 as SEQ ID NO: 39, respectively.

The CH2- and CH3 domains of the immunoglobulin Fc being conjugated to the IgD hinge region may be used without limitation as long as they do not alter pharmacokinetic and drug efficacies of the fusion polypeptide of the present invention, or they do not cause any cytotoxicity such as ADCC and/or CDC, and preferably, the CH2- and CH3 domains of the hybrid Fc of the present invention. Specifically, the CH2- and CH3 domains consisting of amino acid sequences encoded by the amino acid sequence of SEQ ID NO: 29 or the nucleic acid sequence of SEQ ID NO: 40 may be used.

The GLP or analogs thereof and an immunoglobulin Fc polypeptide including the IgD hinge region and the CH2- and CH3 domains are conjugated and thereby the fusion polypeptide of the present invention can be constituted.

For example, when GLP-1 is included in the fusion polypeptide of the present invention, the fusion polypeptide may be one consisting of an amino acid sequence selected from the group consisting of SEQ ID NOs: 30 to 32, and more specifically, one consisting of an amino acid sequence of SEQ ID NO: 30 or 31, or one consisting of an amino acid sequence of SEQ ID NO: 31, although not limited thereto. The amino acid sequence of SEQ ID NO: 30 is in a form where the GLP-1 analog of SEQ ID NO: 2 of the present invention, the IgD hinge region of SEQ ID NO: 26, and the CH2- and CH3 domains of SEQ ID NO: 29 are conjugated to each other, and is indicated as "GLP-1-hyFc8". The amino acid sequence of SEQ ID NO: 31 is in a form where the GLP-1 analog of SEQ ID NO: 2 of the present invention, the IgD hinge region of SEQ ID NO: 27, and the CH2- and CH3 domains of SEQ ID NO: 29 are conjugated to each other, and is indicated as "GLP-1-hyFc9". The amino acid sequence of SEQ ID NO: 32 is in a form where the GLP-1 analog of SEQ ID NO: 2 of the present invention, the IgD hinge region of SEQ ID NO: 28, and the CH2- and CH3 domains of SEQ ID NO: 29 are conjugated to each other, and is indicated as "GLP-1-hyFc11".

Additionally, in another exemplary embodiment of the present invention, when GLP-2 is included in the fusion polypeptide of the present invention, the fusion polypeptide may be one consisting of an amino acid sequence selected from the group consisting of SEQ ID NOs: 47 to 49, and more specifically, one consisting of an amino acid sequence of SEQ ID NO: 48 or 49, or one consisting of an amino acid sequence of SEQ ID NO: 49, although not limited thereto. The amino acid sequence of SEQ ID NO: 47 is in a form where the GLP-2 analog of SEQ ID NO: 45 of the present invention, the IgD hinge region of SEQ ID NO: 26, and the CH2- and CH3 domains of SEQ ID NO: 29 are conjugated to each other, and is indicated as "GLP-2-hyFc8". The amino acid sequence of SEQ ID NO: 48 is in a form where the GLP-2 analog of SEQ ID NO: 45 of the present invention, the IgD hinge region of SEQ ID NO: 27, and the CH2- and CH3 domains of SEQ ID NO: 29 are conjugated to each other, and is indicated as "GLP-2-hyFc9". The amino acid sequence of SEQ ID NO: 49 is in a form where the GLP-2 analog of SEQ ID NO: 45 of the present invention, the IgD hinge region of SEQ ID NO: 28, and the CH2- and CH3 domains of SEQ ID NO: 29 are conjugated to each other, and is indicated as "GLP-2-hyFc11".

In an exemplary embodiment of the present invention, GLP-1-hyFc5 was first prepared by conjugating the hyFc5, which includes the IgD hinge region consisting of a 30 amino acid sequence developed previously by the present inventors, to a GLP-1 (FIG. 1). The half-life of GLP-1-hyFc5 was shown to increase when compared with that of the conventional peptide with GLP-1 alone. However, it was confirmed that the effect of half-life increase shown when the hyFc5 was applied to a GLP-1, which is a short peptide, was not as high as the effects exhibited when the hyFc5 was applied to a large protein.

Accordingly, the present inventors, while endeavoring to find an immunoglobulin Fc polypeptide which shows an improved efficacy compared to that of the hyFc5 when applied to a GLP-1, have discovered that, in the case of a short peptide such as a GLP-1 or a GLP-2, the increase of hinge region length enables the preparation of a fusion polypeptide having excellent activity along with excellent half-life. That is, there is a protease-sensitive cleavage site vulnerable to protease degradation in the IgD hinge region, and when the size of the physiological protein to be conjugated to the immunoglobulin Fc polypeptide was big the cleavage site was not exposed thus causing no problems. However, in the case of a short peptide such as the GLP-1 or GLP-2, the cleavage site was exposed and thus there was no sufficient increase in half-life as expected. Nevertheless, it was confirmed that the increase in hinge region length could solve the problem.

As such, in an exemplary embodiment of the present invention, hyFc9, which includes an IgD hinge region consisting of a 40 amino acid sequence, was prepared (FIG. 2). Based on this, the hyFc8 including an IgD hinge region consisting of a 35 amino acid sequence and the hyFc11 including an IgD hinge region consisting of a 49 amino acid sequence were prepared, and finally, GLP-1-hyFc9-, GLP-1-hyFc8-, and GLP-1-hyFc11 fusion polypeptides were prepared. Additionally, as the measurement result of the PK profiles of the thus-prepared fusion polypeptides of the present invention, these fusion polypeptides were shown to have significantly improved half-lives compared to that of the peptide with GLP-1 alone, and even compared to that of GLP-1-hyFc5 (FIGS. 5 and 6), and thus they were expected to show more effective drug efficacies.

Additionally, when GLP-1-hyFc9, as the representative fusion polypeptide among the fusion polypeptides, was compared in various effects to that of the conventional GLP-1-hyFc5, GLP-1-hyFc9 was shown to be excellent in all aspects including serum stability (FIG. 7), DPP-4 resistance (FIG. 8), and PD profile (FIG. 9). Additionally, GLP-1-hyFc9 was also shown to be excellent regarding the effect of reducing body weight (FIG. 10).

Additionally, in an exemplary embodiment of the present invention, when GLP-1-hyFc9 was compared regarding the effect of ADCC inhibition compared to that of GLP-1-linker-IgG4-mut (U.S. Pat. No. 7,452,966 B2), it was confirmed that GLP-1-hyFc9 has a higher effect of ADCC inhibition than GLP-1-linker-IgG4-mut (FIG. 11). In fact, although GLP-1-linker-IgG4-mut was the one in which modifications were applied to some amino acids of an immunoglobulin Fc for the purpose of preventing ADCC, GLP-1-hyFc9 of the present invention was shown to have much higher inhibitory activity against ADCC.

Additionally, in an exemplary embodiment of the present invention, fusion polypeptides were prepared for GLP-2, in the same manner as in GLP-1. Specifically, GLP-2-hyFc9 including an IgD hinge region consisting of a 40 amino acid sequence was prepared (FIG. 3), and based on this, the GLP-2-hyFc8 including an IgD hinge region consisting of a 35 amino acid sequence and the GLP-2-hyFc11 including an IgD hinge region consisting of a 49 amino acid sequence were prepared. GLP-2-hyFc9 among the thus-prepared fusion polypeptides was shown to have an increased half-life compared to that of the GLP-2-hyFc5 (Examples 2 to 4).

Additionally, in another exemplary embodiment of the present invention, the various biological activities of GLP-2-hyFc9 were examined, and as a result, it was confirmed that GLP-2-hyFc9 does not reduce cAMP activity, which can reduce inflammation (FIG. 12), and was shown to have excellent effects of treating inflammatory bowel disease (FIG. 13), inducing the proliferation of intestinal epithelial cells (FIG. 14), promoting the growth of small intestine (FIG. 15), reducing diarrhea and lethality (FIGS. 16 and 17), etc. In particular, GLP-2-hyFc9 was shown to maintain excellent effect even with a lesser amount compared to that of the comparison group.

In conclusion, it is evident from the foregoing results, that the fusion polypeptides of the present invention have increased half-lives compared to those of the conventional GLP-1 or GLP-2, and in particular, the fusion polypeptides including the GLP-1 have excellent hypoglycemic effect, body weight reducing effect, and resistance to DPP-4 enzyme and thus they can be effectively used for treating diabetes, whereas the fusion polypeptides including the GLP-2 have an intestinotrophic effect and thus can be effectively used for treating inflammatory bowel disease, endoenteritis or diarrhea caused by anticancer chemotherapy, or short bowel syndrome, etc.

Accordingly, in another aspect, the present invention provides a pharmaceutical composition for treating diabetes containing the fusion polypeptide as an active ingredient, and a pharmaceutical composition for treating inflammatory bowel disease, endoenteritis or diarrhea caused by anticancer chemotherapy, or short bowel syndrome, containing the fusion polypeptide as an active ingredient.

Additionally, in still another aspect, the present invention provides a use of the fusion polypeptide for the preparation of a pharmaceutical drug for treating diabetes, inflammatory bowel disease, endoenteritis or diarrhea caused by anticancer chemotherapy, or short bowel syndrome.

Additionally, in still another aspect, the present invention provides a method for treating diabetes, inflammatory bowel disease, endoenteritis or diarrhea caused by anticancer chemotherapy, or short bowel syndrome, including administering the pharmaceutical composition to a subject in need thereof.

In particular, the diabetes may be type 2 diabetes, and the inflammatory bowel disease may be ulcerative colitis or Crohn's disease.

Additionally, the endoenteritis or diarrhea may be induced by anticancer chemotherapy, and in particular, the anticancer chemotherapy may include any chemotherapy without limitation as long as the chemotherapy can induce endoenteritis or diarrhea, e.g., 5-fluorouracil (5-FU), irinotecan, leucovorin, oxaliplatin, etc.

In an exemplary embodiment, the fusion polypeptide of the present invention may be effectively used for treating diabetes by containing GLP-1 or analogs thereof, which have been known as a therapeutic agent for treating diabetes. Additionally, due to the increased half-life, excellent hypoglycemic effect, and increased resistance to DPP-4 enzyme, the fusion polypeptide of the present invention has improved drug profiles compared to those of conventional drugs and thus can be applied to pharmaceutical drugs.

Additionally, in another exemplary embodiment, the fusion polypeptide of the present invention may be effectively used for treating inflammatory bowel disease, endoenteritis or diarrhea caused by anticancer chemotherapy, or short bowel syndrome by containing GLP-2 or analogs thereof, which have been known as a therapeutic agent for treating inflammatory bowel disease, endoenteritis or diarrhea caused by anticancer chemotherapy, or short bowel syndrome, and due to the increased half-life, it has excellent drug profiles compared to those of conventional drugs, it thus can be applied to pharmaceutical drugs.

The fusion polypeptide of the present invention may be used for treating a wide variety of diseases and symptoms.

In an exemplary embodiment, when the GLP included in the fusion polypeptide of the present invention is GLP-1, the fusion polypeptide firstly acts on receptors called "GLP-1 receptors" and thereby exhibits biological effects. Accordingly, subjects, which have diseases and/or symptoms that friendly respond to the stimulation of GLP-1 receptors or administration of GLP-1 compounds may be treated using the fusion polypeptide of the present invention. These subjects are called "require the treatment by GLP-1 compounds" or "need the stimulation of GLP-1 receptors". The subjects who have non-insulin-dependent diabetes, insulin-dependent diabetes, apoplexy (see WO 00/16797), myocardial infarction (see WO 98/08531), obesity (see WO 98/19698), changes after surgery (see U.S. Pat. No. 6,006, 753), functional dyspepsia and irritable bowel syndrome (see WO 99/64060) are included. The subjects (see WO 00/07617) requiring preventative treatment by GLP-1 compounds, for example, those who have the risk of having the non-insulin-dependent diabetes are also included. The subjects who have damaged glucose resistance, damaged fast glucose, those whose body weight accounts for about 25% or more relative to the normal body weight regarding the height and size of the subjects, those who have received a partial pancreatectomy, those who have at least one parent with non-insulin-dependent diabetes, those who have had gestational diabetes, and those who have had acute or chronic pancreatitis have the risk of developing non-insulin-dependent diabetes.

Additionally, in another exemplary embodiment, when the GLP included in the fusion polypeptide of the present invention is GLP-2, the fusion polypeptide may be used to treat and prevent gastrointestinal disorders, for example, for the treatment of osteoporosis, DPP-4 mediated symptoms, newborn infants with damaged intestinal functions, etc. Examples of the gastrointestinal disorders may include ulcer, gastritis, dyspepsia syndrome, short bowel syndrome, cul-de-sac syndrome, inflammatory bowel disease, gluten-induced enteropathy or celiac sprue occurred from chronic dyspepsia, tropical sprue, hypogammaglobulinemia sprue, gastroenteritis, local gastroenteritis (Crohn's disease), ulcerative colitis, diarrhea-associated irritable bowel syndrome, injury of small bowel, short bowel syndrome, endoenteritis caused by anticancer chemotherapy and diarrhea caused by anticancer chemotherapy, etc. Additionally, other symptoms, such as gastroenteritis due to radiation, inflammatory gastroenteritis or gastroenteritis after inflammation, and injury of small bowel by toxic materials or other chemotherapies, may be included.

The effective amount of the fusion polypeptide described in the present invention is the amount that can bring about the intended effects of treatment and/or prevention while not inducing unacceptable adverse effects, when the fusion polypeptide is administered to a subject in need of the stimulation of GLP-1 or GLP-2 receptor. The "intended effect" includes at least one described below: 1) reduction of disease(s) or associated symptom(s) thereof; 2) delay of initiation of signs associated with disease(s) or symptom(s); 3) an increase of life-expectancy compared to that without treatment; and 4) higher quality-life compared to that without treatment. For example, the "effective amount" of the fusion polypeptide of the present invention refers to the amount that can cause a delay in the occurrence of diabetic complications, such as retinopathy, neuropathy, and renal disease, by causing a larger control of blood glucose levels compared to that of the untreated case. The "effective amount" of the fusion polypeptide of the present invention for preventing diabetes refers to the amount that can delay the occurrence of a disease at the increased blood glucose level requiring the treatment with anti-hypoglycemic drugs, such as sulfonyl, urea, thiazolidinedione, insulin and/or bisguanidine, compared to that of the untreated case.

In an exemplary embodiment of the present invention, the fusion polypeptide of the present invention was confirmed to also have excellent drug efficacy for treating diabetes, in addition to the experiment which confirmed the PK profiles confirmed by half-life. Specifically, when the pharmacodynamic (PD) profile of GLP-1-hyFc9 fusion polypeptide was examined in an in-vivo experiment, GLP-1-hyFc9 fusion polypeptide was shown to have much higher hypoglycemic effect compared to that of GLP-1-hyFc5 (FIG. 9), and also in an in-vitro experiment, GLP-1-hyFc9 fusion polypeptide was shown to have significantly higher resistance to DPP-4 enzyme thus confirming that GLP-1-hyFc9 fusion polypeptide has excellent effect with regard to stability to DPP-4 enzyme (FIG. 8). It is thus evident that the maintenance of blood glucose levels is important in treating diabetes, and considering that DPP-4 inhibitor is normally used as a therapeutic agent for treating diabetes, the fusion polypeptide of the present invention can be used as an excellent drug for treating diabetes.

As used herein, the term "treatment" refers to all actions that restore or beneficially change the symptoms of diabetes, inflammatory bowel disease, endoenteritis or diarrhea caused by anticancer chemotherapy, or short bowel syndrome, by administering the fusion polypeptide according to the present invention or a pharmaceutical composition containing the same.

The pharmaceutical composition of the present invention may contain the fusion polypeptide at varied wt % as an active ingredient, as long as it can exhibit the therapeutic effect for treating diabetes, inflammatory bowel disease, endoenteritis or diarrhea caused by anticancer chemotherapy, or short bowel syndrome.

Additionally, the pharmaceutical composition of the present invention may further contain appropriate carriers, excipients, or diluents according to the conventional method. Examples of the carriers, excipients, and diluents to be contained in the composition of the present invention may include lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate, mineral oil, etc., but is not limited thereto.

The pharmaceutical composition of the present invention may be prepared according to the conventional method in a formulation type for oral administration, such as powders, granules, tablets, capsules, suspensions, emulsions, syrups and aerosols; a formulation type for external use; a formulation type for suppositories; or a formulation type for sterile injections. Specifically, the formulations may be prepared using a commonly used diluent or excipient, such as a filler, an extender, a binder, a humectant, a disintegrant, a surfactant, etc. Solid formulations for oral administration may include tablets, pills, powders, granules, capsules, etc., and these solid formulations may be prepared by adding at least one excipient, e.g., starch, calcium carbonate, sucrose or lactose, gelatin, etc. Additionally, a lubricant such as magnesium stearate and talc may be used, in addition to a simple excipient. Examples of liquid formulations for oral administration may include suspensions, liquid medicine for internal use, emulsions, syrups, etc., and various kinds of excipients such as humectants, sweeteners, fragrances, preservatives, etc., may be contained, in addition to the frequently used simple diluents such as water and liquid paraffin. Examples of formulations for parenteral administration may include sterile aqueous solutions, non-aqueous solvents, suspensions, emulsions, lyophilized formulations, and suppositories. For non-aqueous solvents and suspensions, propylene glycol, polyethylene glycol, a vegetable oil such as olive oil, an injectable ester such as ethyloleate may be used. Examples of bases for suppositories may include Witepsol, macrogol, Tween 61, cacao butter, laurinum, glycerogelatin, etc.

The composition of the present invention is administered in a pharmaceutically effective amount. As used herein, the term "pharmaceutically effective amount" refers to an amount sufficient for the treatment of diseases at a reasonable benefit/risk ratio applicable to a medical treatment without causing any adverse effects, and the level of the effective dose may be determined based on the factors including the health conditions of a patient, type of disease(s), severity of illness, drug activity, drug sensitivity, administration method, administration time, administration route and excretion rate, length of treatment, factors including drug(s) to be mixed or concurrently used in combination, and other factors well known in the medical field.

Additionally, the pharmaceutical composition of the present invention may be administered alone or in combination with other therapeutic agent(s), which exhibit(s) therapeutic effects for treating diabetes, inflammatory bowel disease, endoenteritis or diarrhea caused by anticancer chemotherapy, or short bowel syndrome. The pharmaceutical composition of the present invention may be administered in various routes to mammals including rats, mice, cattle, humans, etc. The administration means the introduction of a particular material to a patient by an appropriate manner, and the composition may be administered via any of the common routes as long as the composition can arrive at a target tissue. For example, administration may be performed intraarticularly, intraperitoneally, intravenously, intramuscularly, subcutaneously, intradermally, orally, topically, intranasally, intrapulmonarily, intrarectally, etc., but is not limited thereto.

The fusion polypeptide of the present invention is preferably administered once in four weeks, once in two weeks, or once a week. The fusion polypeptide may be more frequently administered according to the diseases to be treated, e.g., twice or three times a week.

In another aspect, the present invention provides a polynucleotide encoding the fusion polypeptide, an expression vector including the polynucleotide, and a host cell including the expression vector.

The technical feature of the present invention lies in the fusion polypeptide explained above, and the polynucleotide encoding the fusion polypeptide, the expression vector including the polynucleotide, and the host cell including the expression vector may be included within the scope of the present invention, and the type of host cell is not limited as long as the expression of the fusion polypeptide is enabled.

Although not limited thereto, the polynucleotide may be, for example, one which consists of a nucleic acid sequence of SEQ ID NO: 41 encoding 'GLP-1-hyFc8'; one which consists of a nucleic acid sequence of SEQ ID NO: 42 encoding 'GLP-1-hyFc9'; or one which consists of a nucleic acid sequence of SEQ ID NO: 43 encoding 'GLP-1-hyFc11'; and specifically, may be one which consists of a nucleic acid sequence of SEQ ID NO: 41 or SEQ ID NO: 42; or one which consists of a nucleic acid sequence of SEQ ID NO: 42.

Additionally, in another exemplary embodiment, the polynucleotide may be one which consists of a nucleic acid sequence of SEQ ID NO: 52 encoding 'GLP-2-hyFc8'; one which consists of a nucleic acid sequence of SEQ ID NO: 53 encoding 'GLP-2-hyFc9'; or one which consists of a nucleic acid sequence of SEQ ID NO: 54 encoding 'GLP-2-hyFc11'; and specifically, may be one which consists of a nucleic acid sequence of SEQ ID NO: 53 or SEQ ID NO: 54; or one which consists of a nucleic acid sequence of SEQ ID NO: 54.

Considering the codons preferred by organisms to express the fusion polypeptide based on the codon degeneracy, various modifications on the fusion polynucleotide may be executed on the coding region within the scope not changing the amino acid sequence of the fusion polypeptide.

Advantageous Effects of the Invention

The fusion polypeptide of the present invention has an increased half-life and improved resistance to DPP-4 enzyme compared to those of GLP-1 and GLP-2, and thus it has improved drug efficacy in treating diabetes, inflammatory bowel disease, endoenteritis or diarrhea caused by anticancer chemotherapy, or short bowel syndrome, compared to those of the conventional drugs. Accordingly, the fusion polypeptide of the present invention can be effectively applied to pharmaceutical drugs.

BRIEF DESCRIPTION OF THE DRAWINGS

FIG. 3, being related to the preparation of GLP-2-hyFc9, shows a schematic diagram of GLP-2-hyFc5 and GLP-2-hyFc9, respectively.

FIG. 4 shows a graph confirming the PK profiles of GLP-1 peptide and GLP-1-hyFc5.

FIG. 5, being related to the PK profiles of GLP-1-hyFc5 and GLP-1-hyFc9, shows the values of the areas under the curve (AUC) illustrating the amount of proteins remaining in the blood and drug concentration in each time zone.

FIG. 6, being related to the PK profiles of GLP-1-hyFc5, GLP-1-hyFc8, and GLP-1-hyFc9, shows the amount of proteins remaining in the blood in each time zone.

FIG. 7, being related to the confirmation of serum stability of GLP-1-hyFc5 and GLP-1-hyFc9, shows the values of the areas under the curve (AUC) of a graph illustrating the amount of proteins remaining in the blood in each time zone.

FIG. 8, being related to the confirmation of DPP-4 resistibility of GLP-1-hyFc5 and GLP-1-hyFc9, shows the values of the areas under the curve (AUC) of a graph illustrating the amount of proteins remaining in the blood in each reaction time zone.

FIG. 9, being related to the confirmation of PD profiles of GLP-1-hyFc5 and GLP-1-hyFc9, shows the AUC values obtained by measuring the change in glucose concentration in the blood as AUC content % relative to that of negative control.

FIG. 10, being related to the confirmation of body weight loss effect of GLP-1-hyFc9, shows the amount of body weight change and the cumulative food intake.

FIG. 11, being related to the comparison results of ADCC-inhibitory effects of GLP-1-hyFc9 and GLP-1-linker-IgG4-mut, confirms their binding capabilities to Fcγ receptors.

FIG. 12, being related to the confirmation of in-vitro biological activities of GLP-2, GLP-2-hyFc5, and GLP-2-hyFc9, shows the measurement results of membrane depolarization induced by cAMP.

FIG. 13, being related to the therapeutic effects of GLP-2-2G and GLP-2-hyFc9 on inflammatory bowel disease, shows the changes in body weight, amount of TNF-α expression, and length of small intestine in an experimental model induced with inflammatory bowel disease by Indomethacin administration.

FIG. 14 confirms the effects of GLP-2-2G and GLP-2-hyFc9 on inducing the proliferation of intestinal epithelial cells.

FIG. 15, being related to the confirmation of the effect of GLP-2-hyFc9 on the growth promotion of small intestine, shows the weight of small intestine.

FIG. 16, being related to the confirmation of the effect of GLP-2-hyFc9 on the reduction of diarrhea induced by 5-FU.

FIG. 17, being related to the confirmation of the effect of GLP-2-hyFc9 on the reduction of lethality, shows the decreased morbidity rate occurred due to the induction of diarrhea by 5-FU.

DETAILED DESCRIPTION OF THE INVENTION

Hereinafter, the present invention will be described in more detail with reference to the following Examples. However, these Examples are for illustrative purposes only, and the invention is not intended to be limited by these Examples.

Example 1: Preparation of GLP-hyFc Fusion Protein 1-1: Preparation of GLP-1-hyFc5, GLP-1-hyFc9, GLP-1-hyFc8, and GLP-1-hyFc11

Although glucagon like peptide-1 (GLP-1) is a protein effective for the treatment of diabetes, it had many limitations to be developed as a drug because it is very rapidly cleaved in-vivo by DPP-4 enzyme and has a very short half-life of about 3 to 5 minutes, and thus many attempts have been made to increase in-vivo half-life.

Figure 1:
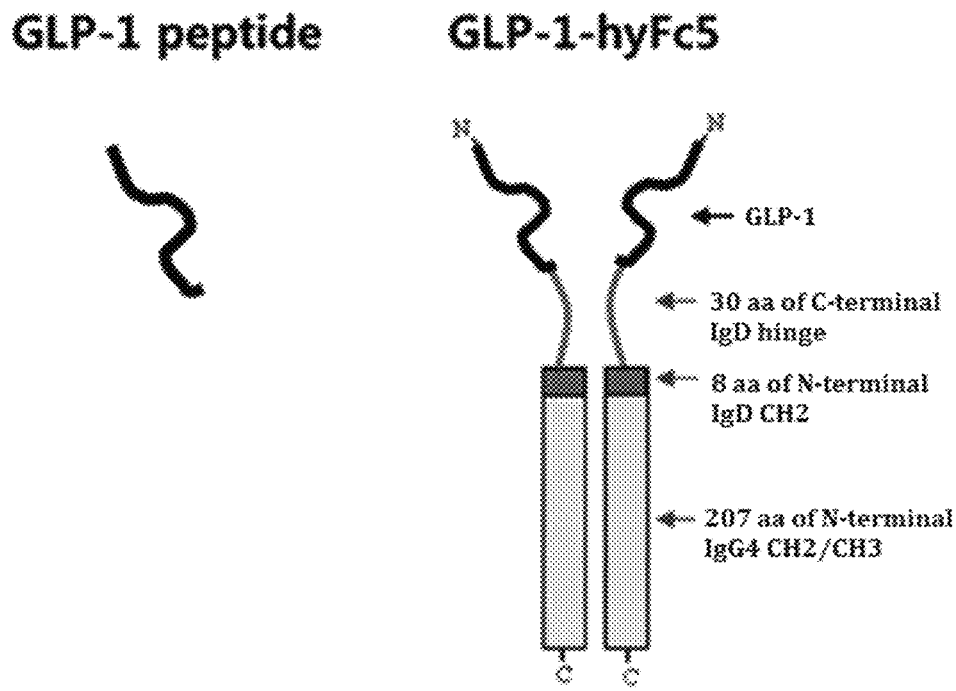
FIG. 1, being related to the preparation of GLP-1-hyFc5, shows a schematic diagram and a sequence of GLP-1-hyFc5.

As such, in order to reduce the cleavage by DPP-4 enzyme, a GLP-1 analog was prepared based on GLP-1 (7-37) by substituting alanine, the amino acid at position 8, which is the cleavage site for DPP-4 enzyme, with glycine (SEQ ID NO: 2). Then, GLP-1-hyFc5 fusion polypeptide was prepared by fusing the hybrid Fc 5 (hyFc5) polypeptide, which was previously prepared in International Patent Publication No. WO 2008-147143 by the present inventors, to the GLP-1 analog peptide (FIG. 1). The entire sequence of GLP-1-hyFc5 fusion polypeptide is shown in FIG. 1.

Additionally, in the present invention, it was attempted to prepare a fusion polypeptide having excellent activities in other aspects while further increasing the half-life compared to that of GLP-1-hyFc5.

Specifically, it was attempted to prepare a fusion polypeptide having excellent activities while having an improved half-life by variously controlling the IgD hinge region of hyFc5, and it was confirmed that the increase of the number of amino acids at the IgD hinge region could satisfy these conditions.

Figure 2:
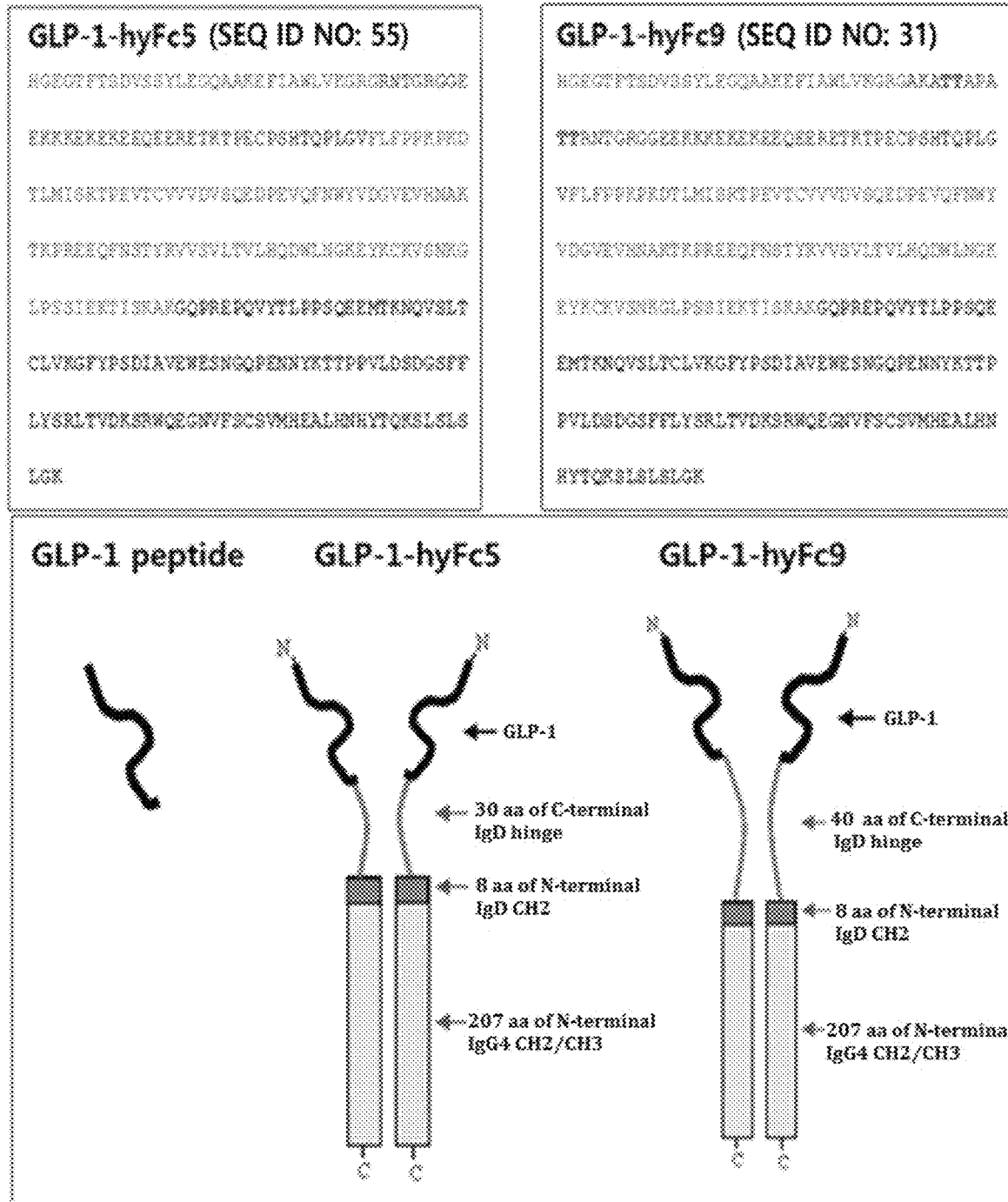
FIG. 2, being related to the preparation of GLP-1-hyFc9, shows a sequence and a schematic diagram of GLP-1-hyFc5 and GLP-1-hyFc9, respectively.

Accordingly, hyFc9 (FIG. 2), which has a hinge region consisting of 40 amino acids (SEQ ID NO: 27) was first prepared by increasing the number of amino acids in the hinge region of the hyFc5, which has a hinge region consisting of 30 amino acids, and then the hyFc8, which has a hinge region consisting of 35 amino acids (SEQ ID NO: 26), and the hyFc11, which has a hinge region consisting of 49 amino acids (SEQ ID NO: 28) were prepared, respectively. Additionally, GLP-1-hyFc9 (SEQ ID NO: 31), GLP-1-hyFc8 (SEQ ID NO: 30), and GLP-1-hyFc11 (SEQ ID NO: 32) fusion polypeptides were prepared by conjugating the GLP-1 analog peptide to each of hyFc9, the hyFc8, and the hyFc11, respectively.

1-2: Preparation of GLP-2-hyFc5, GLP-2-hyFc9, GLP-2-hyFc8, and GLP-2-hyFc11

As is the case with GLP-1, glucagon like peptide-2 (GLP-2) also had many limitations to be developed as a drug because it is very rapidly cleaved in-vivo by DPP-4 enzyme and has a very short half-life of about 7 minutes. In order to increase the in-vivo half-life of GLP-2, alanine, the amino acid at position 2, which is the cleavage site for DPP-4 enzyme, is substituted with glycine (GLP-2-2G peptide, SEQ ID NO: 45). Although the substituted GLP-2-2G peptide is prepared in a once-daily formulation for treating short bowel syndrome in adults, it is still necessary to develop a GLP-2 analog having a much longer half-life than the substituted GLP-2-2G peptide, considering that short bowel syndrome should be treated continuously. For this purpose, GLP-2-hyFc5 fusion polypeptide was prepared by fusing the hyFc5 polypeptide, which was previously prepared in International Patent Publication No. WO 2008-147143 by the present inventors, to GLP-2-2G analog peptide (FIG. 3). Additionally, it was attempted to prepare a fusion polypeptide having excellent activities while having an improved half-life by variously controlling the IgD hinge region with the entire length of 64 amino acids. Specifically, hyFc9, which has a hinge region consisting of 40 amino acids, was prepared by increasing the amino acids in the hinge region of the hyFc5, which has a hinge region consisting of 30 amino acids, and then GLP-2-hyFc9 fusion polypeptide was prepared by conjugating GLP-2-2G peptide thereto (FIG. 3, SEQ ID NO: 48). Additionally, the hyFc8, which has a hinge region consisting of 35 amino acids, and the hyFc11, which has a hinge region consisting of 49 amino acids, were prepared, and then GLP-2-hyFc8 (SEQ ID NO: 47) and GLP-2-hyFc11 (SEQ ID NO: 49) fusion polypeptides were prepared by conjugating GLP-2-2G peptide to each of them Example 2: Confirmation of PK Profile of GLP-hyFc Fusion Protein 2-1: Confirmation of PK Profile of GLP-1-hyFc5

In order to confirm the pharmacokinetic profile (PK profile) of the thus-prepared GLP-1-hyFc5 fusion polypeptide, experiments were performed as follows using the synthesized GLP-1 as a control.

Male Sprague Dawley rats (4 rats/group) were administered intravenously with respective proteins, GLP-1 and GLP-1-hyFc5. Blood samples were collected before the administration and after the administration at 0.08-, 0.16-, 0.5-, 1-, 2-, 4-, 6-, 12-, 24-, 48-, 72-, and 96 hours, respectively. The blood samples were stored at room temperature for 30 minutes for agglutination. The samples were centrifuged at 3000 rpm for 10 minutes to obtain serum from each sample and then stored in a deep freezer. The samples were quantitated by dilution to be analyzed in a position on a straight line of standard curve using GLP-1 kit (ALPCO, Cat. No. 43-GP1HU-E01).

As a result, as shown in FIG. 4, the peptide including GLP-1 alone, which was not fused with the hyFc polypeptide, had a short half-life of 4 minutes, whereas GLP-1-hyFc5 polypeptide, which was fused with GLP-1 and hyFc5, was shown to have a half-life with about a 116-fold increase (>8 hours).

2-2: Confirmation of PK Profile GLP-1-hyFc9

The PK profile was confirmed by comparing the half-life of GLP-1-hyFc9 fusion polypeptide with that of GLP-1-hyFc5 fusion polypeptide prepared in Example 1.

Male Sprague Dawley rats (4 rats/group) were administered subcutaneously with respective proteins. Blood samples were collected before the administration and after the administration at 2-, 6-, 12-, 26-, 48-, 72-, 96-, 120-, 144-, and 168 hours, respectively. The blood samples were stored at room temperature for 30 minutes for agglutination. The samples were centrifuged at 3000 rpm for 10 minutes to obtain serum from each sample and then stored in a deep freezer. The samples were quantitated by dilution to be analyzed in a position on a straight line of standard curve using GLP-1 kit (IBL, Cat. No. 27784A).

The results were indicated in terms of protein amount remaining in the blood for each time zone and the value of the area under the curve (AUC). As shown in FIG. 5, GLP-1-hyFc9 had about a 12-fold higher AUC value compared to that of GLP-1-hyFc5. Based on these results, GLP-1-hyFc9 was confirmed to have a significantly increased half-life compared to that of GLP-1-hyFc5, and is thus expected to have more effective drug efficacy.

2-3: Confirmation of PK Profile GLP-1-hyFc8

The PK profile of the GLP-1-hyFc8 fusion polypeptide was confirmed by comparing the half-life of the GLP-1-hyFc8 fusion polypeptide with that of GLP-1-hyFc9 fusion polypeptide. Experiments were performed for GLP-1-hyFc5, the GLP-1-hyFc9, and the GLP-1-hyFc8 in the same manner as in Example 2-2.

As a result, as shown in FIG. 6, GLP-1-hyFc9 and the GLP-1-hyFc8 were confirmed to have a similar level of PK profiles, and the GLP-1-hyFc8 showed a slightly higher level. These levels were shown to be much higher levels compared to that of the control, GLP-1-hyFc5. Based on these results, the GLP-1-hyFc8 was confirmed to have more effective drug efficacy with the increased half-life.

2-4: Confirmation of PK Profiles of GLP-2-hyFc5 and GLP-2-hyFc9

In order to confirm the pharmacokinetic profiles (PK profiles) of the GLP-2-hyFc5 and GLP-2-hyFc9 fusion polypeptides prepared above, experiments were performed as follows.

Male Sprague Dawley rats (3 rats/group) were administered subcutaneously with respective proteins (GLP-2-2G peptide, GLP-2-hyFc5, and GLP-2-hyFc9). Blood samples were collected before the administration and after the administration at 0.08-, 0.16-, 0.5-, 2-, 4-, 8-, 24-, 48-, 96-, 120-, and 168 hours, respectively. The blood samples were stored at room temperature for 30 minutes for agglutination. The samples were centrifuged at 3000 rpm for 10 minutes to obtain serum from each sample and then stored in a deep freezer. The samples were quantitated by dilution to be analyzed in a position on a straight line of standard curve using GLP-2 kit (Millipore, Cat. No. EZGLP2-37K). As a result, the peptide including GLP-2-2G peptide alone, which was not fused with an Fc protein, had a short half-life of 1.2 hours, whereas the GLP-2-hyFc5 and GLP-2-hyFc9 fusion proteins were shown to have half-lives of 44- and 65 hours, respectively, thus showing about a 36- and 54-fold increase, compared to that of GLP-2-2G. In particular, GLP-2-hyFc9 was shown to have about a 1.5-fold increase compared to that of the GLP-2-hyFc5.

Example 3: Test of Biological Activity of GLP-hyFc Fusion Protein 3-1: Confirmation of Serum Stability of GLP-1-hyFc9

Additional various effects of GLP-1-hyFc9, among the fusion polypeptides with excellent PK profiles, were confirmed. GLP-1-hyFc5 was used as a comparison group. In order to confirm the stability of GLP-1-hyFc5 and GLP-1-hyFc9 on the decomposing factors in sera, the stability test was performed in rat sera.

First, two test materials were diluted with rat sera, and each sample was reacted at 37° C. for 0-, 6-, 10-, 24-, and 48 hours, and each material was quantitated via ELISA assay.

The results were indicated in terms of protein amount remaining in the blood for each time zone and the value of the area under the curve (AUC). As shown in FIG. 7, GLP-1-hyFc9 had about a 1.2-fold higher AUC value compared to that of GLP-1-hyFc5. Based on these results, GLP-1-hyFc9 was confirmed to also have a significantly higher serum stability compared to that of GLP-1-hyFc5.

3-2: Confirmation of DPP-4 Resistance of GLP-1-hyFc9

DPP-4 resistance test was performed in order to confirm the resistance of GLP-1-hyFc5 and GLP-1-hyFc9 to DPP-4 (Sigma, Cat No. D4943-1VL), which is a major metabolic enzyme, and the subsequent stability thereof.

Two test materials were added into a thermostat kept at 37° C., reacted for 0-, 2-, 8-, 24-, and 48 hours, and each material was quantitated.

The results were indicated in terms of protein amount remaining in the blood for each time zone and the value of the area under the curve (AUC). As shown in FIG. 8, GLP-1-hyFc9 had about a 7-fold higher DPP-4 resistance compared to that of GLP-1-hyFc5. Based on these results, GLP-1-hyFc9 was confirmed to have a significantly increased stability to DPP-4 enzyme, which can cleave GLP-1).

3-3: Confirmation of PD Profile of GLP-1-hyFc9

In order to confirm the pharmacokinetic profiles (PK profiles) of GLP-1-hyFc5 and GLP-1-hyFc9, experiments were performed as follows.

CD-1 mice (10 mice/group) were administered subcutaneously with the respective proteins and then administered with glucose on day 0, 1, 2, 4, and 8 thereafter and the change in blood glucose levels was measured to confirm the hypoglycemic effect.

Regarding the result, the change in blood glucose levels was measured at each measurement date from 1 minute to 180 minutes after the glucose administration and the AUC values were obtained for each experiment day, and indicated as the AUC content (%) of GLP-1-hyFc5 and GLP-1-hyFc9 relative to the negative control (vehicle).

As a result, as shown in FIG. 9, it was confirmed that GLP-1-hyFc5 started to lose the hypoglycemic effect from the Day 2 and became normalized, whereas GLP-1-hyFc9 maintained the blood glucose levels up to the Day 8 at a low level. These results indicate that GLP-1-hyFc9 can retain hypoglycemic effect until the Day 8.

3-4: Confirmation of the Weight-Reducing Effect of GLP-1-hyFc9

The pharmacokinetic disposition (PD, cumulative food intake & weight loss effect) of GLP-1-hyFc9 in an ob/ob disease model was confirmed relative to the negative control (vehicle).

The ob/ob mice (10 mice/group) were repeatedly administered subcutaneously once a week with the protein and the changes in body weight and cumulative food intake were measured each week. For body weight, the difference obtained by subtracting the value of change in body weight of the negative control from the value of change in body weight per group is indicated, and for cumulative food intake, likewise, the difference relative to that of the negative control is indicated (FIG. 10). Consequently, GLP-1-hyFc9 exhibited a significant effect of body weight loss and the effect of reducing food intake in terms of the change in body weight and cumulative food intake, compared to that of the negative control, and that the effects were in a dose-dependent manner.

In summary, as shown in Table 2 below, GLP-1-hyFc9 was shown to have improved effects compared to GLP-1-hyFc5.

TABLE 2

|  |  | hyFc5 | hyFc9 |
|---|---|---|---|
| In-vitro | Serum stability (rat) | ++ | +++ |
|  | DPP-4 resistibility | + | ++++ |
| In-vivo | PK study (rat) | + | ++++ |
|  | IPGTT (mouse) | + | +++ |

3-5: Comparison of ADCC Inhibitory Activity with GLP-1-Linker-IgG4-Mut

Additionally, for GLP-1-hyFc9 fusion polypeptide exhibiting excellent effects in various aspects through examples, the superiorities were confirmed by comparing the ADCC inhibitory with that of the fusion polypeptides known in the art.

GLP-1-linker-IgG4-mut disclosed in U.S. Pat. No. 7,452,966 B2 was used as a comparison group, which is a polypeptide intended to inhibit antibody dependent cell-mediated cytotoxicity (ADCC) due to three mutations in the IgG4 region.

Since both GLP-1-linker-IgG4-mut and GLP-1-hyFc9 of the present invention structurally include the CH2-CH3 domains of the IgG4, there is no safety issue regarding complement dependent cytotoxicity (CDC) involved therein. However, for confirming the ADCC safety, the binding affinity to the Fcγ receptors, which serve an important role in inducing ADCC, and for this purpose, a test of binding affinity was performed using Surface Plasmon Resonance (SPR, Bio-rad, #Proteon XPR36).

First, ligands were immobilized by flowing Fcγ receptors into each channel of bio-rad chips, which were amine-coupled by an NHS/EDC reaction, using an acetate buffer. As the concept of the negative control, a phosphate buffered saline (PBS) containing Tween 20 was flown. Each of the chips, to which each Fcγ receptor was bound, was measured of its binding affinity by flowing each test material thereto.

As a result, as shown in FIG. 11, GLP-1-linker-IgG4-mut showed higher binding capability to major Fcγ receptors, which induce ADCC, although several amino acid sites were modified in order to remove the remaining effector functions of the immunoglobulin Fc region, compared to GLP-1-hyFc9, and for this reason, it was confirmed to have potential cytotoxicity. In contrast, GLP-1-hyFc9 showed lower binding ability with all Fcγ receptors compared to GLP-1-linker-IgG4-mut, and from this, GLP-1-hyFc9 was confirmed to be safer in the case of a long-term drug administration.

3-6: Test of Inflammation-Associated Biological Activity of GLP-2-hyFc9

Along with GLP-1-hyFc9, GLP-2-hyFc9 was subjected to a biological activity test. Since GLP-2-hyFc9, although having a significantly increased half-life, can reduce the biological activity of GLP-2-2G peptide itself due to the fusion with hyFc9, the biological activity was examined.

In order to examine the biological activity of GLP-2-hyFc9, the level of intracellular cAMP, which is increased upon the stimulation of GLP-2-hyFc9. The GLP-2R-expressing 293 cells were cultured in a 96-well in an amount of $6 \times 10^4$ cells. In 24 hours, the cells were treated with the fusion proteins at concentrations of 0 nM, 0.1 nM, 1 nM, 3 nM, 10 nM, 100 nM, and 300 nM, and the membrane depolarization induced by the increased intracellular cAMP was measured using a fluorescent membrane potential dye. As a result, as shown in FIG. 12, it was confirmed that the GLP-2-hyFc5 fusion protein was markedly reduced in its biological activity by showing an activity of 27% when the activity of GLP-2-2G peptide was set at 100%, whereas GLP-2-hyFc9 fusion protein showed an activity of 98% thus showing no reduction in its inflammation-related biological activity, even after the fusion with hyFc9.

3-7: Confirmation of the Therapeutic Effect of GLP-2-hyFc9 on Inflammatory Bowel Disease GLP-2-hyFc9 was subcutaneously administered to an inflammatory bowel disease model induced by Indomethacin and the effect of improvement was compared. Male Sprague Dawley rats (6 rats/group) were treated with Indomethacin on Day 1 and Day 2 at a concentration of 9 mg/kg to induce inflammatory bowel disease. GLP-2-2G, as a comparison group, was administered twice daily to a total of 12 times at a concentration of 50 nmol/kg from Day 3 to Day 8, whereas GLP-2-hyFc9 was administered once every two days to a total of 3 times at a concentration of 50 nmol/kg and the rats were autopsied on Day 9. The changes in the body weight, the length of small intestine, and the expression level of inflammatory cytokine (TNF-α) were compared in each group, and the therapeutic effects on the symptoms of inflammatory bowel disease were compared.

As a result, as shown in FIG. 13, the body weight and the length of small intestine were shown to significantly decrease while the expression level of inflammatory cytokine (TNF-α) increased by Indomethacin treatment. However, in the group treated with GLP-2-hyFc9 showed a lower reduction in the body weight, a decrease in the expression level of inflammatory cytokine (TNF-α), and also an increase in the length of small intestine, thus confirming the therapeutic effect of GLP-2-hyFc9 on the treatment of inflammatory bowel disease. In particular, GLP-2-hyFc9, although administered at a level of one-fourth to that of GLP-2-2G, showed a more significant effect.

3-8: Confirmation of the Effect of GLP-2-hyFc on Inducing the Proliferation of Intestinal Epithelial Cells The effect of GLP-2-hyFc9 on inducing the proliferation of intestinal epithelial cells was examined. GLP-2-2G peptide was used as a comparison group. GLP-2 is known to increase the production of growth factors (IGF-1, VEGF, EGF, etc.) by acting on fibroblasts (effector cells), and the increased growth factors promote the proliferation of intestinal epithelial cells. Accordingly, an experiment was performed to confirm the effect of GLP-2-hyFc9 on inducing the proliferation of intestinal epithelial cells. CCD-18co cells were cultured in a serum-free medium for 24 hours, treated with GLP-2-2G and GLP-2-hyFc9 at concentrations of 50 nM, 100 nM, and 250 nM, and cultured for 24 hours. Caco-2 cells were treated with the cell culture medium (conditioned media; CM), cultured for 3 days, and Caco-2 cell proliferation was measured using EZ Cytox (Dogen, Cat. No. EZ-1000). As a result, as shown in FIG. 14, the capability of GLP-2-hyFc9 of promoting Caco-2 cell proliferation was similar to that of GLP-2-2G peptide. That is, the biological activity of GLP-2, even after a fusion with hyFc9, was shown to be maintained at a level similar to that of native GLP-2.

3-9: Confirmation of the Intestinotrophic Effect of GLP-2-hyFc9

In order to confirm the pharmacodynamic characteristic of GLP-2-hyFc9, i.e., intestinotrophic effect, an experiment was performed as follows. Male Sprague Dawley rats (8 rats/group) were treated with GLP-2-hyFc9 once daily for 5 days at concentrations of 0 nmol/kg, 1 nmol/kg, 3 nmol/kg, 10 nmol/kg, 30 nmol/kg, 100 nmol/kg, and 300 nmol/kg, autopsied to measure the weight of their small intestine, and thereby the intestinotrophic effect of GLP-2-hyFc9 was confirmed. As shown in FIG. 15, the group treated with GLP-2-hyFc9 showed an increase of small intestine in a dose-dependent manner, and $ED_{50}$ was shown to be 14.2 nmol/kg/day.

3-10: Confirmation of the Effect of GLP-2-hyFc9 on Reducing Diarrhea and Lethality Irinotecan or 5-FU, among the anticancer chemotherapy drugs used for killing cancer cells, can induce villous atrophy by destroying crypts cells, which form the villi of intestinal cells, and this may lead to fatal diarrhea. Since the villous atrophy and diarrhea induced by anticancer chemotherapy drugs may affect lethality, an experiment was performed to confirm whether the GLP-2-hyFc9 treatment can prevent diarrhea and lethality induced by anticancer chemotherapy drugs. Male Sprague Dawley rats (15 rats/group) were treated with 5-FU once daily to a total of four times at a concentration of 75 mg/kg to induce diarrhea. The rats were treated with GLP-2-hyFc a total of four times at a concentration of 80 nmol/kg/day or once at a concentration of 320 nmol/kg/day, and diarrhea score was examined for 10 days, thereby confirming lethality. As a result, as shown in FIG. 16, the group treated four times with GLP-2-hyFc9 at a concentration of 80 nmol/kg/day showed a decrease in diarrhea score compared to the untreated group, and the group treated once with GLP-2-hyFc9 at a concentration of 320 nmol/kg/day showed a significant decrease in diarrhea score compared to the group treated four times with GLP-2-hyFc9 at a low dose. Additionally, the lethality induced by 5-FU (27%) was reduced by 20% to 6.7% in the group treated with GLP-2-hyFc9 (FIG. 17). Therefore, it was confirmed that GLP-2-hyFc9 has the effect of preventing diarrhea induced by anticancer chemotherapy.

The invention claimed is:

1. A fusion polypeptide comprising (a) glucagon-like peptide-1 (GLP-1) or an analog thereof, and (b) an immunoglobulin Fc polypeptide,
   wherein the immunoglobulin Fc polypeptide (b) comprises
   (i) an isolated IgD hinge region consisting of 35 to 49 consecutive amino acid residues from the C-terminus of SEQ ID NO: 25; and
   (ii) a CH2 domain and a CH3 domain of the immunoglobulin Fc polypeptide.

2. The fusion polypeptide of claim 1, wherein the GLP-1 consists of an amino acid sequence of SEQ ID NO: 1 or SEQ ID NO: 13.

3. The fusion polypeptide of claim 1, wherein the analog of the GLP-1 comprises a modification in a site, which may be cleaved by DPP-4 enzyme, and consists of the amino acid sequence selected from the group consisting of SEQ ID NOs: 2 to 12 and SEQ ID NOs: 14 to 24.

4. The fusion polypeptide of claim 1, wherein the IgD hinge region consists of the amino acid sequence selected from the group consisting of SEQ ID NOs: 26 to 28.

5. The fusion polypeptide of claim 1, wherein the fusion polypeptide exhibits an increased half-life compared to the polypeptide which is not fused with the immunoglobulin Fc polypeptide.

6. The fusion polypeptide of claim 1, wherein the fusion polypeptide consists of the amino acid sequence selected from the group consisting of SEQ ID NOs: 30 to 32.

7. A pharmaceutical composition comprising the fusion polypeptide of claim 1 as an active ingredient.

8. A method for treating diabetes comprising administering the pharmaceutical composition of claim 7 to a subject in need thereof.

9. A polynucleotide encoding the fusion polypeptide according to claim 1.

10. The polynucleotide of claim 9, wherein the polynucleotide consists of the nucleic acid sequence selected from the group consisting of SEQ ID NOs: 41 to 43.

11. An expression vector comprising the polynucleotide of claim 9.

12. A host cell comprising the expression vector of claim 11.

* * * * *

SEQUENCE LISTING

<160> NUMBER OF SEQ ID NOS: 55

<210> SEQ ID NO 1
<211> LENGTH: 31
<212> TYPE: PRT
<213> ORGANISM: Homo sapiens

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 2
<211> LENGTH: 31
<212> TYPE: PRT
<213> ORGANISM: Artificial Sequence
<220> FEATURE:
<223> OTHER INFORMATION: GLP-1(7-37) analogue (A8G)

<400> SEQUENCE: 2

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 3
<211> LENGTH: 31
<212> TYPE: PRT
<213> ORGANISM: Artificial Sequence
<220> FEATURE:
<223> OTHER INFORMATION: GLP-1(7-37) analogue (A8V)

<400> SEQUENCE: 3

His Val Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 4
<211> LENGTH: 31
<212> TYPE: PRT
<213> ORGANISM: Artificial Sequence
<220> FEATURE:
<223> OTHER INFORMATION: GLP-1(7-37) analogue (G22E)

<400> SEQUENCE: 4

His Ala Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Arg Gly
            20                  25                  30

<210> SEQ ID NO 5
<211> LENGTH: 31
<212> TYPE: PRT
<213> ORGANISM: Artificial Sequence
<220> FEATURE:
<223> OTHER INFORMATION: GLP-1(7-37) analogue (R36G)

<400> SEQUENCE: 5

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Gly Gly
            20                  25                  30

```
<210> SEQ ID NO 6
<211> LENGTH: 31
<212> TYPE: PRT
<213> ORGANISM: Artificial Sequence
<220> FEATURE:
<223> OTHER INFORMATION: GLP-1(7-37) analogue (A8G/G22E)

<400> SEQUENCE: 6

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Arg Gly
            20                  25                  30

<210> SEQ ID NO 7
<211> LENGTH: 31
<212> TYPE: PRT
<213> ORGANISM: Artificial Sequence
<220> FEATURE:
<223> OTHER INFORMATION: GLP-1(7-37) analogue (A8V/G22E)

<400> SEQUENCE: 7

His Val Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Arg Gly
            20                  25                  30

<210> SEQ ID NO 8
<211> LENGTH: 31
<212> TYPE: PRT
<213> ORGANISM: Artificial Sequence
<220> FEATURE:
<223> OTHER INFORMATION: GLP-1(7-37) analogue (A8G/R36G)

<400> SEQUENCE: 8

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Gly Gly
            20                  25                  30

<210> SEQ ID NO 9
<211> LENGTH: 31
<212> TYPE: PRT
<213> ORGANISM: Artificial Sequence
<220> FEATURE:
<223> OTHER INFORMATION: GLP-1(7-37) analogue (A8V/R36G)

<400> SEQUENCE: 9

His Val Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Gly Gly
            20                  25                  30

<210> SEQ ID NO 10
<211> LENGTH: 31
<212> TYPE: PRT
<213> ORGANISM: Artificial Sequence
<220> FEATURE:
<223> OTHER INFORMATION: GLP-1(7-37) analogue (G22E/R36G)

<400> SEQUENCE: 10

His Ala Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly
            20                  25                  30
```

<210> SEQ ID NO 11
<211> LENGTH: 31
<212> TYPE: PRT
<213> ORGANISM: Artificial Sequence
<220> FEATURE:
<223> OTHER INFORMATION: GLP-1(7-37) analogue (A8G/G22E/R36G)

<400> SEQUENCE: 11

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly
            20                  25                  30

<210> SEQ ID NO 12
<211> LENGTH: 31
<212> TYPE: PRT
<213> ORGANISM: Artificial Sequence
<220> FEATURE:
<223> OTHER INFORMATION: GLP-1(7-37) analogue (A8V/G22E/R36G)

<400> SEQUENCE: 12

His Val Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly
            20                  25                  30

<210> SEQ ID NO 13
<211> LENGTH: 30
<212> TYPE: PRT
<213> ORGANISM: Homo sapiens

<400> SEQUENCE: 13

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 14
<211> LENGTH: 30
<212> TYPE: PRT
<213> ORGANISM: Artificial Sequence
<220> FEATURE:
<223> OTHER INFORMATION: GLP-1(7-36) analogue (A8G)

<400> SEQUENCE: 14

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 15
<211> LENGTH: 30
<212> TYPE: PRT
<213> ORGANISM: Artificial Sequence
<220> FEATURE:
<223> OTHER INFORMATION: GLP-1(7-36) analogue (A8V)

<400> SEQUENCE: 15

His Val Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

```
<210> SEQ ID NO 16
<211> LENGTH: 30
<212> TYPE: PRT
<213> ORGANISM: Artificial Sequence
<220> FEATURE:
<223> OTHER INFORMATION: GLP-1(7-36) analogue (G22E)

<400> SEQUENCE: 16

His Ala Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Arg
            20                  25                  30

<210> SEQ ID NO 17
<211> LENGTH: 30
<212> TYPE: PRT
<213> ORGANISM: Artificial Sequence
<220> FEATURE:
<223> OTHER INFORMATION: GLP-1(7-36) analogue (R36G)

<400> SEQUENCE: 17

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Gly
            20                  25                  30

<210> SEQ ID NO 18
<211> LENGTH: 30
<212> TYPE: PRT
<213> ORGANISM: Artificial Sequence
<220> FEATURE:
<223> OTHER INFORMATION: GLP-1(7-36) analogue (A8G/G22E)

<400> SEQUENCE: 18

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Arg
            20                  25                  30

<210> SEQ ID NO 19
<211> LENGTH: 30
<212> TYPE: PRT
<213> ORGANISM: Artificial Sequence
<220> FEATURE:
<223> OTHER INFORMATION: GLP-1(7-36) analogue (A8V/G22E)

<400> SEQUENCE: 19

His Val Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Arg
            20                  25                  30

<210> SEQ ID NO 20
<211> LENGTH: 30
<212> TYPE: PRT
<213> ORGANISM: Artificial Sequence
<220> FEATURE:
<223> OTHER INFORMATION: GLP-1(7-36) analogue (A8G/R36G)

<400> SEQUENCE: 20

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Gly
```

-continued

```
                    20                  25                  30

<210> SEQ ID NO 21
<211> LENGTH: 30
<212> TYPE: PRT
<213> ORGANISM: Artificial Sequence
<220> FEATURE:
<223> OTHER INFORMATION: GLP-1(7-36) analogue (A8V/R36G)

<400> SEQUENCE: 21

His Val Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Gly
            20                  25                  30

<210> SEQ ID NO 22
<211> LENGTH: 30
<212> TYPE: PRT
<213> ORGANISM: Artificial Sequence
<220> FEATURE:
<223> OTHER INFORMATION: GLP-1(7-36) analogue (G22E/R36G)

<400> SEQUENCE: 22

His Ala Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly
            20                  25                  30

<210> SEQ ID NO 23
<211> LENGTH: 30
<212> TYPE: PRT
<213> ORGANISM: Artificial Sequence
<220> FEATURE:
<223> OTHER INFORMATION: GLP-1(7-36) analogue (A8G/G22E/R36G)

<400> SEQUENCE: 23

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly
            20                  25                  30

<210> SEQ ID NO 24
<211> LENGTH: 30
<212> TYPE: PRT
<213> ORGANISM: Artificial Sequence
<220> FEATURE:
<223> OTHER INFORMATION: GLP-1(7-36) analogue (A8V/G22E/R36G)

<400> SEQUENCE: 24

His Val Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly
            20                  25                  30

<210> SEQ ID NO 25
<211> LENGTH: 64
<212> TYPE: PRT
<213> ORGANISM: Homo sapiens

<400> SEQUENCE: 25

Arg Trp Pro Glu Ser Pro Lys Ala Gln Ala Ser Ser Val Pro Thr Ala
1               5                   10                  15

Gln Pro Gln Ala Glu Gly Ser Leu Ala Lys Ala Thr Thr Ala Pro Ala
            20                  25                  30
```

Thr Thr Arg Asn Thr Gly Arg Gly Gly Glu Lys Lys Lys Glu Lys
            35                  40                  45

Glu Lys Glu Glu Gln Glu Arg Glu Thr Lys Thr Pro Glu Cys Pro
    50                  55                  60

<210> SEQ ID NO 26
<211> LENGTH: 35
<212> TYPE: PRT
<213> ORGANISM: Homo sapiens

<400> SEQUENCE: 26

Ala Pro Ala Thr Thr Arg Asn Thr Gly Arg Gly Gly Glu Lys Lys
1               5                   10                  15

Lys Glu Lys Glu Lys Glu Glu Gln Glu Arg Glu Thr Lys Thr Pro
            20                  25                  30

Glu Cys Pro
        35

<210> SEQ ID NO 27
<211> LENGTH: 40
<212> TYPE: PRT
<213> ORGANISM: Homo sapiens

<400> SEQUENCE: 27

Ala Lys Ala Thr Thr Ala Pro Ala Thr Thr Arg Asn Thr Gly Arg Gly
1               5                   10                  15

Gly Glu Glu Lys Lys Lys Glu Lys Glu Glu Gln Glu Arg
            20                  25                  30

Glu Thr Lys Thr Pro Glu Cys Pro
        35                  40

<210> SEQ ID NO 28
<211> LENGTH: 49
<212> TYPE: PRT
<213> ORGANISM: Homo sapiens

<400> SEQUENCE: 28

Ala Gln Pro Gln Ala Glu Gly Ser Leu Ala Lys Ala Thr Thr Ala Pro
1               5                   10                  15

Ala Thr Thr Arg Asn Thr Gly Arg Gly Gly Glu Glu Lys Lys Lys Glu
            20                  25                  30

Lys Glu Lys Glu Glu Gln Glu Glu Arg Glu Thr Lys Thr Pro Glu Cys
        35                  40                  45

Pro

<210> SEQ ID NO 29
<211> LENGTH: 215
<212> TYPE: PRT
<213> ORGANISM: Artificial Sequence
<220> FEATURE:
<223> OTHER INFORMATION: IgD & IgG4 Hybrid CH2 &CH3 region

<400> SEQUENCE: 29

Ser His Thr Gln Pro Leu Gly Val Phe Leu Phe Pro Pro Lys Pro Lys
1               5                   10                  15

Asp Thr Leu Met Ile Ser Arg Thr Pro Glu Val Thr Cys Val Val Val
            20                  25                  30

Asp Val Ser Gln Glu Asp Pro Glu Val Gln Phe Asn Trp Tyr Val Asp
        35                  40                  45

```
Gly Val Glu Val His Asn Ala Lys Thr Lys Pro Arg Glu Glu Gln Phe
     50                  55                  60

Ala Ser Thr Tyr Arg Val Val Ser Val Leu Thr Val Leu His Gln Asp
 65                  70                  75                  80

Trp Leu Asn Gly Lys Glu Tyr Lys Cys Lys Val Ser Asn Lys Gly Leu
                 85                  90                  95

Pro Ser Ser Ile Glu Lys Thr Ile Ser Lys Ala Lys Gly Gln Pro Arg
                100                 105                 110

Glu Pro Gln Val Tyr Thr Leu Pro Pro Ser Gln Glu Met Thr Lys
             115                 120                 125

Asn Gln Val Ser Leu Thr Cys Leu Val Lys Gly Phe Tyr Pro Ser Asp
 130                 135                 140

Ile Ala Val Glu Trp Glu Ser Asn Gly Gln Pro Glu Asn Asn Tyr Lys
 145                 150                 155                 160

Thr Thr Pro Pro Val Leu Asp Ser Asp Gly Ser Phe Phe Leu Tyr Ser
                165                 170                 175

Arg Leu Thr Val Asp Lys Ser Arg Trp Gln Gly Asn Val Phe Ser
             180                 185                 190

Cys Ser Val Met His Glu Ala Leu His Asn His Tyr Thr Gln Lys Ser
                195                 200                 205

Leu Ser Leu Ser Leu Gly Lys
 210                 215

<210> SEQ ID NO 30
<211> LENGTH: 281
<212> TYPE: PRT
<213> ORGANISM: Artificial Sequence
<220> FEATURE:
<223> OTHER INFORMATION: GLP-1-hyFc8

<400> SEQUENCE: 30

His Gly Glu Gly Thr Phe Thr Ser Asp Val Ser Ser Tyr Leu Glu Gly
  1               5                  10                  15

Gln Ala Ala Lys Glu Phe Ile Ala Trp Leu Val Lys Gly Arg Gly Ala
                 20                  25                  30

Pro Ala Thr Thr Arg Asn Thr Gly Arg Gly Gly Glu Glu Lys Lys Lys
                 35                  40                  45

Glu Lys Glu Lys Glu Glu Gln Glu Glu Arg Glu Thr Lys Thr Pro Glu
     50                  55                  60

Cys Pro Ser His Thr Gln Pro Leu Gly Val Phe Leu Phe Pro Pro Lys
 65                  70                  75                  80

Pro Lys Asp Thr Leu Met Ile Ser Arg Thr Pro Glu Val Thr Cys Val
                 85                  90                  95

Val Val Asp Val Ser Gln Glu Asp Pro Glu Val Gln Phe Asn Trp Tyr
                100                 105                 110

Val Asp Gly Val Glu Val His Asn Ala Lys Thr Lys Pro Arg Glu Glu
             115                 120                 125

Gln Phe Asn Ser Thr Tyr Arg Val Val Ser Val Leu Thr Val Leu His
 130                 135                 140

Gln Asp Trp Leu Asn Gly Lys Glu Tyr Lys Cys Lys Val Ser Asn Lys
145                 150                 155                 160

Gly Leu Pro Ser Ser Ile Glu Lys Thr Ile Ser Lys Ala Lys Gly Gln
                165                 170                 175

Pro Arg Glu Pro Gln Val Tyr Thr Leu Pro Pro Ser Gln Glu Glu Met
             180                 185                 190
```

```
Thr Lys Asn Gln Val Ser Leu Thr Cys Leu Val Lys Gly Phe Tyr Pro
            195                 200                 205

Ser Asp Ile Ala Val Glu Trp Glu Ser Asn Gly Gln Pro Glu Asn Asn
        210                 215                 220

Tyr Lys Thr Thr Pro Pro Val Leu Asp Ser Asp Gly Ser Phe Phe Leu
225                 230                 235                 240

Tyr Ser Arg Leu Thr Val Asp Lys Ser Arg Trp Gln Glu Gly Asn Val
                245                 250                 255

Phe Ser Cys Ser Val Met His Glu Ala Leu His Asn His Tyr Thr Gln
            260                 265                 270

Lys Ser Leu Ser Leu Ser Leu Gly Lys
            275                 280

<210> SEQ ID NO 31
<211> LENGTH: 286
<212> TYPE: PRT
<213> ORGANISM: Artificial Sequence
<220> FEATURE:
<223> OTHER INFORMATION: GLP-1-hyFc9

<400> SEQUENCE: 31

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly Ala
            20                  25                  30

Lys Ala Thr Thr Ala Pro Ala Thr Thr Arg Asn Thr Gly Arg Gly Gly
        35                  40                  45

Glu Glu Lys Lys Lys Glu Lys Glu Lys Glu Gln Glu Glu Arg Glu
    50                  55                  60

Thr Lys Thr Pro Glu Cys Pro Ser His Thr Gln Pro Leu Gly Val Phe
65                  70                  75                  80

Leu Phe Pro Pro Lys Pro Lys Asp Thr Leu Met Ile Ser Arg Thr Pro
                85                  90                  95

Glu Val Thr Cys Val Val Val Asp Val Ser Gln Glu Asp Pro Glu Val
            100                 105                 110

Gln Phe Asn Trp Tyr Val Asp Gly Val Glu Val His Asn Ala Lys Thr
        115                 120                 125

Lys Pro Arg Glu Glu Gln Phe Asn Ser Thr Tyr Arg Val Val Ser Val
    130                 135                 140

Leu Thr Val Leu His Gln Asp Trp Leu Asn Gly Lys Glu Tyr Lys Cys
145                 150                 155                 160

Lys Val Ser Asn Lys Gly Leu Pro Ser Ser Ile Glu Lys Thr Ile Ser
                165                 170                 175

Lys Ala Lys Gly Gln Pro Arg Glu Pro Gln Val Tyr Thr Leu Pro Pro
            180                 185                 190

Ser Gln Glu Glu Met Thr Lys Asn Gln Val Ser Leu Thr Cys Leu Val
        195                 200                 205

Lys Gly Phe Tyr Pro Ser Asp Ile Ala Val Glu Trp Glu Ser Asn Gly
    210                 215                 220

Gln Pro Glu Asn Asn Tyr Lys Thr Thr Pro Pro Val Leu Asp Ser Asp
225                 230                 235                 240

Gly Ser Phe Phe Leu Tyr Ser Arg Leu Thr Val Asp Lys Ser Arg Trp
                245                 250                 255

Gln Glu Gly Asn Val Phe Ser Cys Ser Val Met His Glu Ala Leu His
            260                 265                 270
```

```
Asn His Tyr Thr Gln Lys Ser Leu Ser Leu Ser Leu Gly Lys
            275                 280                 285
```

<210> SEQ ID NO 32
<211> LENGTH: 295
<212> TYPE: PRT
<213> ORGANISM: Artificial Sequence
<220> FEATURE:
<223> OTHER INFORMATION: GLP-1-hyFc11

<400> SEQUENCE: 32

```
His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly Ala
            20                  25                  30

Gln Pro Gln Ala Glu Gly Ser Leu Ala Lys Ala Thr Thr Ala Pro Ala
        35                  40                  45

Thr Thr Arg Asn Thr Gly Arg Gly Gly Glu Glu Lys Lys Lys Glu Lys
    50                  55                  60

Glu Lys Glu Glu Gln Glu Glu Arg Glu Thr Lys Thr Pro Glu Cys Pro
65                  70                  75                  80

Ser His Thr Gln Pro Leu Gly Val Phe Leu Phe Pro Pro Lys Pro Lys
                85                  90                  95

Asp Thr Leu Met Ile Ser Arg Thr Pro Glu Val Thr Cys Val Val Val
            100                 105                 110

Asp Val Ser Gln Glu Asp Pro Glu Val Gln Phe Asn Trp Tyr Val Asp
        115                 120                 125

Gly Val Glu Val His Asn Ala Lys Thr Lys Pro Arg Glu Glu Gln Phe
    130                 135                 140

Asn Ser Thr Tyr Arg Val Val Ser Val Leu Thr Val Leu His Gln Asp
145                 150                 155                 160

Trp Leu Asn Gly Lys Glu Tyr Lys Cys Lys Val Ser Asn Lys Gly Leu
                165                 170                 175

Pro Ser Ser Ile Glu Lys Thr Ile Ser Lys Ala Lys Gly Gln Pro Arg
            180                 185                 190

Glu Pro Gln Val Tyr Thr Leu Pro Pro Ser Gln Glu Glu Met Thr Lys
        195                 200                 205

Asn Gln Val Ser Leu Thr Cys Leu Val Lys Gly Phe Tyr Pro Ser Asp
    210                 215                 220

Ile Ala Val Glu Trp Glu Ser Asn Gly Gln Pro Glu Asn Asn Tyr Lys
225                 230                 235                 240

Thr Thr Pro Pro Val Leu Asp Ser Asp Gly Ser Phe Phe Leu Tyr Ser
                245                 250                 255

Arg Leu Thr Val Asp Lys Ser Arg Trp Gln Glu Gly Asn Val Phe Ser
            260                 265                 270

Cys Ser Val Met His Glu Ala Leu His Asn His Tyr Thr Gln Lys Ser
        275                 280                 285

Leu Ser Leu Ser Leu Gly Lys
    290                 295
```

<210> SEQ ID NO 33
<211> LENGTH: 93
<212> TYPE: DNA
<213> ORGANISM: Homo sapiens

<400> SEQUENCE: 33

```
cacgccgaag gcaccttcac cagcgacgtg agcagctacc tggaaggcca ggctgccaag    60
```

```
gagttcatcg cctggctggt gaaaggcaga ggc                                    93
```

<210> SEQ ID NO 34
<211> LENGTH: 93
<212> TYPE: DNA
<213> ORGANISM: Artificial Sequence
<220> FEATURE:
<223> OTHER INFORMATION: GLP-1(7-37) analogue (A8G)

<400> SEQUENCE: 34

```
cacggcgaag gcaccttcac cagcgacgtg agcagctacc tggaaggcca ggctgccaag      60
gagttcatcg cctggctggt gaaaggcaga ggc                                    93
```

<210> SEQ ID NO 35
<211> LENGTH: 90
<212> TYPE: DNA
<213> ORGANISM: Homo sapiens

<400> SEQUENCE: 35

```
cacgccgaag gcaccttcac cagcgacgtg agcagctacc tggaaggcca ggctgccaag      60
gagttcatcg cctggctggt gaaaggcaga                                        90
```

<210> SEQ ID NO 36
<211> LENGTH: 192
<212> TYPE: DNA
<213> ORGANISM: Homo sapiens

<400> SEQUENCE: 36

```
agatggcccg agagccctaa ggcccaggcc agctccgtgc ccacagctca gccacaggct      60
gagggaagcc tcgccaaggc aacgactgcg ccggccacta cgcgcaacac cggccgcggc     120
ggcgaggaga agaagaagga aaggagaag gaggagcagg aggagcgcga gaccaagacc     180
cccgagtgcc cc                                                          192
```

<210> SEQ ID NO 37
<211> LENGTH: 105
<212> TYPE: DNA
<213> ORGANISM: Homo sapiens

<400> SEQUENCE: 37

```
gcgccggcca ctacgcgcaa caccggccgc ggcggcgagg agaagaagaa ggagaaggag      60
aaggaggagc aggaggagcg cgagaccaag accccccgagt gcccc                    105
```

<210> SEQ ID NO 38
<211> LENGTH: 120
<212> TYPE: DNA
<213> ORGANISM: Homo sapiens

<400> SEQUENCE: 38

```
gccaaggcaa cgactgcgcc ggccactacg cgcaacaccg gccgcggcgg cgaggagaag      60
aagaaggaga aggagaagga ggagcaggag gagcgcgaga ccaagacccc cgagtgcccc     120
```

<210> SEQ ID NO 39
<211> LENGTH: 147
<212> TYPE: DNA
<213> ORGANISM: Homo sapiens

<400> SEQUENCE: 39

```
gctcagccac aggctgaggg aagcctcgcc aaggcaacga ctgcgccggc cactacgcgc      60
```

```
aacaccggcc gcggcggcga ggagaagaag aaggagaagg agaaggagga gcaggaggag    120
cgcgagacca agacccccga gtgcccc                                        147

<210> SEQ ID NO 40
<211> LENGTH: 645
<212> TYPE: DNA
<213> ORGANISM: Artificial Sequence
<220> FEATURE:
<223> OTHER INFORMATION: IgD & IgG4 Hybrid CH2 & CH3 region

<400> SEQUENCE: 40
agccacaccc agcccctggg cgtgttcctg ttccccccca gcccaaggac accctgatg    60 atcagccgca ccccccgaggt gacctgcgtg gtcgtggatg tgagccagga agatcccgaa    120
gtgcagttca actggtacgt ggatggcgtg gaagtgcaca acgccaagac caagcccaga    180
gaagagcagt tcaactccac ctacagagtg gtgagcgtgc tgaccgtgct gcaccaggac    240
tggctgaacg gcaaggagta caagtgcaag gtgtccaaca aaggcctgcc cagctccatc    300
gagaagacca tcagcaaagc caaggccagc ccagagaaac ccaggtgta caccctgcct    360 cccagccagg aagagatgac caagaaccag gtgtccctga cctgcctggt gaaaggcttc    420
taccccagcg acatcgccgt ggagtgggaa agcaacggcc agcccgagaa caattacaag    480 acaaccctc ccgtgctgga tagcgatggc agcttctttc tgtacagcag actgaccgtg    540
gacaagagca gatggcagga aggcaacgtg ttcagctgca gcgtgatgca cgaagccctg    600
cacaaccact acacccagaa gagcctgtcc ctgagcctgg gcaag                   645

<210> SEQ ID NO 41
<211> LENGTH: 843
<212> TYPE: DNA
<213> ORGANISM: Artificial Sequence
<220> FEATURE:
<223> OTHER INFORMATION: GLP-1-hyFc8

<400> SEQUENCE: 41
cacggcgaag gcaccttcac cagcgacgtg agcagctacc tggaaggcca ggctgccaag    60
gagttcatcg cctggctggt gaaaggcaga ggcgcgccgg ccactacgcg caacaccggc    120
cgcggcggcg aggagaagaa gaaggagaag gagaaggagg agcaggagga gcgcgagacc    180 aagaccccccg agtgccccag ccacacccag cccctgggcg tgttcctgtt ccccccaag    240 cccaaggaca ccctgatgat cagccgcacc cccgaggtga cctgcgtggt cgtggatgtg    300
agccaggaag atcccgaagt gcagttcaac tggtacgtgg atggcgtgga agtgcacaac    360
gccaagacca gcccagaga gagcagttc aactccacct acagagtggt gagcgtgctg    420
accgtgctgc accaggactg gctgaacggc aaggagtaca agtgcaaggt gtccaacaaa    480
ggcctgccca gctccatcga gaagaccatc agcaaagcca aggccagcc cagagaaccc    540 caggtgtaca ccctgcctcc cagccaggaa gagatgacca agaaccaggt gtccctgacc    600
tgcctggtga aaggcttcta ccccagcgac atcgccgtgg agtgggaaag caacggccag    660
cccgagaaca attacaagac aaccccctccc gtgctggata gcgatggcag cttctttctg    720
tacagcagac tgaccgtgga caagagcaga tggcaggaag gcaacgtgtt cagctgcagc    780
gtgatgcacg aagccctgca caaccactac acccagaaga gcctgtccct gagcctgggc    840
aag                                                                  843

<210> SEQ ID NO 42
<211> LENGTH: 858
```

<212> TYPE: DNA
<213> ORGANISM: Artificial Sequence
<220> FEATURE:
<223> OTHER INFORMATION: GLP-1-hyFc9

<400> SEQUENCE: 42

```
cacggcgaag gcaccttcac cagcgacgtg agcagctacc tggaaggcca ggctgccaag      60
gagttcatcg cctggctggt gaaaggcaga ggcgccaagg caacgactgc gccggccact     120
acgcgcaaca ccggccgcgg cggcgaggag aagaagaagg agaaggagaa ggaggagcag     180
gaggagcgcg agaccaagac ccccgagtgc ccagccaca cccagccccct gggcgtgttc     240
ctgttccccc ccaagcccaa ggacaccctg atgatcagcc gcaccccga ggtgacctgc     300
gtggtcgtgg atgtgagcca ggaagatccc gaagtgcagt tcaactggta cgtggatggc     360
gtggaagtgc acaacgccaa gaccaagccc agagaagagc agttcaactc cacctacaga     420
gtggtgagcg tgctgaccgt gctgcaccag gactggctga acggcaagga gtacaagtgc     480
aaggtgtcca acaaaggcct gcccagctcc atcgagaaga ccatcagcaa agccaaaggc     540
cagcccagag aaccccaggt gtacaccctg cctcccagcc aggaagagat gaccaagaac     600
caggtgtccc tgacctgcct ggtgaaaggc ttctacccca gcgacatcgc cgtggagtgg     660
gaaagcaacg gccagcccga gaacaattac aagacaaccc ctcccgtgct ggatagcgat     720
ggcagcttct ttctgtacag cagactgacc gtggacaaga gcagatggca ggaaggcaac     780
gtgttcagct gcagcgtgat gcacgaagcc ctgcacaacc actacaccca gaagagcctg     840
tccctgagcc tgggcaag                                                   858
```

<210> SEQ ID NO 43
<211> LENGTH: 885
<212> TYPE: DNA
<213> ORGANISM: Artificial Sequence
<220> FEATURE:
<223> OTHER INFORMATION: GLP-1-hyFc11

<400> SEQUENCE: 43

```
cacggcgaag gcaccttcac cagcgacgtg agcagctacc tggaaggcca ggctgccaag      60
gagttcatcg cctggctggt gaaaggcaga ggcgctcagc acaggctga gggaagcctc     120
gccaaggcaa cgactgcgcc ggccactacg cgcaacaccg gccgcggcgg cgaggagaag     180
aagaaggaga aggagaagga ggagcaggag gagcgcgaga ccaagacccc cgagtgcccc     240
agccacaccc agccccctggg cgtgttcctg ttccccccca gcccaaggac accctgatg     300
atcagccgca cccccgaggt gacctgcgtg gtcgtggatg tgagccagga agatcccgaa     360
gtgcagttca actggtacgt ggatggcgtg gaagtgcaca acgccaagac caagcccaga     420
gaagagcagt tcaactccac ctacagagtg gtgagcgtgc tgaccgtgct gcaccaggac     480
tggctgaacg gcaaggagta caagtgcaag gtgtccaaca aaggcctgcc cagctccatc     540
gagaagacca tcagcaaagc caaggccag cccagagaac ccaggtgta cacctgcct     600
cccagccagg aagagatgac caagaaccag gtgtccctga cctgcctggt gaaaggcttc     660
taccccagcg acatcgccgt ggagtgggaa agcaacggcc agcccgagaa caattacaag     720
acaaccccctc ccgtgctgga tagcgatggc agcttctttc tgtacagcag actgaccgtg     780
gacaagagca gatggcagga aggcaacgtg ttcagctgca gcgtgatgca cgaagccctg     840
cacaaccact acacccagaa gagcctgtcc ctgagcctgg gcaag                     885
```

<210> SEQ ID NO 44

```
<211> LENGTH: 33
<212> TYPE: PRT
<213> ORGANISM: Homo sapiens

<400> SEQUENCE: 44

His Ala Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp

<210> SEQ ID NO 45
<211> LENGTH: 33
<212> TYPE: PRT
<213> ORGANISM: Artificial Sequence
<220> FEATURE:
<223> OTHER INFORMATION: GLP-2 analogue (A2G)

<400> SEQUENCE: 45

His Gly Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp

<210> SEQ ID NO 46
<211> LENGTH: 33
<212> TYPE: PRT
<213> ORGANISM: Artificial Sequence
<220> FEATURE:
<223> OTHER INFORMATION: GLP-2 analogue (A2V)

<400> SEQUENCE: 46

His Val Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp

<210> SEQ ID NO 47
<211> LENGTH: 283
<212> TYPE: PRT
<213> ORGANISM: Artificial Sequence
<220> FEATURE:
<223> OTHER INFORMATION: GLP-2-hyFc8

<400> SEQUENCE: 47

His Gly Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp Ala Pro Ala Thr Thr Arg Asn Thr Gly Arg Gly Gly Glu Glu Lys
                35                  40                  45

Lys Lys Glu Lys Glu Lys Glu Glu Gln Glu Glu Arg Glu Thr Lys Thr
        50                  55                  60

Pro Glu Cys Pro Ser His Thr Gln Pro Leu Gly Val Phe Leu Phe Pro
65                  70                  75                  80

Pro Lys Pro Lys Asp Thr Leu Met Ile Ser Arg Thr Pro Glu Val Thr
                85                  90                  95

Cys Val Val Val Asp Val Ser Gln Glu Asp Pro Glu Val Gln Phe Asn
```

```
                100                 105                 110
Trp Tyr Val Asp Gly Val Glu Val His Asn Ala Lys Thr Lys Pro Arg
            115                 120                 125

Glu Glu Gln Phe Asn Ser Thr Tyr Arg Val Val Ser Val Leu Thr Val
130                 135                 140

Leu His Gln Asp Trp Leu Asn Gly Lys Glu Tyr Lys Cys Lys Val Ser
145                 150                 155                 160

Asn Lys Gly Leu Pro Ser Ser Ile Glu Lys Thr Ile Ser Lys Ala Lys
                165                 170                 175

Gly Gln Pro Arg Glu Pro Gln Val Tyr Thr Leu Pro Pro Ser Gln Glu
            180                 185                 190

Glu Met Thr Lys Asn Gln Val Ser Leu Thr Cys Leu Val Lys Gly Phe
        195                 200                 205

Tyr Pro Ser Asp Ile Ala Val Glu Trp Glu Ser Asn Gly Gln Pro Glu
        210                 215                 220

Asn Asn Tyr Lys Thr Thr Pro Pro Val Leu Asp Ser Asp Gly Ser Phe
225                 230                 235                 240

Phe Leu Tyr Ser Arg Leu Thr Val Asp Lys Ser Arg Trp Gln Glu Gly
            245                 250                 255

Asn Val Phe Ser Cys Ser Val Met His Glu Ala Leu His Asn His Tyr
            260                 265                 270

Thr Gln Lys Ser Leu Ser Leu Ser Leu Gly Lys
            275                 280

<210> SEQ ID NO 48
<211> LENGTH: 288
<212> TYPE: PRT
<213> ORGANISM: Artificial Sequence
<220> FEATURE:
<223> OTHER INFORMATION: GLP-2-hyFc9

<400> SEQUENCE: 48

His Gly Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp Ala Lys Ala Thr Thr Ala Pro Ala Thr Thr Arg Asn Thr Gly Arg
        35                  40                  45

Gly Gly Glu Glu Lys Lys Lys Glu Lys Glu Lys Glu Glu Gln Glu Glu
    50                  55                  60

Arg Glu Thr Lys Thr Pro Glu Cys Pro Ser His Thr Gln Pro Leu Gly
65                  70                  75                  80

Val Phe Leu Phe Pro Pro Lys Pro Lys Asp Thr Leu Met Ile Ser Arg
                85                  90                  95

Thr Pro Glu Val Thr Cys Val Val Val Asp Val Ser Gln Glu Asp Pro
            100                 105                 110

Glu Val Gln Phe Asn Trp Tyr Val Asp Gly Val Glu Val His Asn Ala
        115                 120                 125

Lys Thr Lys Pro Arg Glu Glu Gln Phe Asn Ser Thr Tyr Arg Val Val
    130                 135                 140

Ser Val Leu Thr Val Leu His Gln Asp Trp Leu Asn Gly Lys Glu Tyr
145                 150                 155                 160

Lys Cys Lys Val Ser Asn Lys Gly Leu Pro Ser Ser Ile Glu Lys Thr
                165                 170                 175

Ile Ser Lys Ala Lys Gly Gln Pro Arg Glu Pro Gln Val Tyr Thr Leu
```

```
                180                 185                 190
Pro Pro Ser Gln Glu Glu Met Thr Lys Asn Gln Val Ser Leu Thr Cys
            195                 200                 205

Leu Val Lys Gly Phe Tyr Pro Ser Asp Ile Ala Val Glu Trp Glu Ser
        210                 215                 220

Asn Gly Gln Pro Glu Asn Asn Tyr Lys Thr Thr Pro Pro Val Leu Asp
225                 230                 235                 240

Ser Asp Gly Ser Phe Phe Leu Tyr Ser Arg Leu Thr Val Asp Lys Ser
                245                 250                 255

Arg Trp Gln Glu Gly Asn Val Phe Ser Cys Ser Val Met His Glu Ala
            260                 265                 270

Leu His Asn His Tyr Thr Gln Lys Ser Leu Ser Leu Ser Leu Gly Lys
        275                 280                 285

<210> SEQ ID NO 49
<211> LENGTH: 297
<212> TYPE: PRT
<213> ORGANISM: Artificial Sequence
<220> FEATURE:
<223> OTHER INFORMATION: GLP-2-hyFc11

<400> SEQUENCE: 49

His Gly Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp Ala Gln Pro Gln Ala Glu Gly Ser Leu Ala Lys Ala Thr Thr Ala
        35                  40                  45

Pro Ala Thr Thr Arg Asn Thr Gly Arg Gly Gly Glu Glu Lys Lys Lys
    50                  55                  60

Glu Lys Glu Lys Glu Glu Gln Glu Arg Glu Thr Lys Thr Pro Glu
65                  70                  75                  80

Cys Pro Ser His Thr Gln Pro Leu Gly Val Phe Leu Phe Pro Pro Lys
                85                  90                  95

Pro Lys Asp Thr Leu Met Ile Ser Arg Thr Pro Glu Val Thr Cys Val
            100                 105                 110

Val Val Asp Val Ser Gln Glu Asp Pro Glu Val Gln Phe Asn Trp Tyr
        115                 120                 125

Val Asp Gly Val Glu Val His Asn Ala Lys Thr Lys Pro Arg Glu Glu
    130                 135                 140

Gln Phe Asn Ser Thr Tyr Arg Val Val Ser Val Leu Thr Val Leu His
145                 150                 155                 160

Gln Asp Trp Leu Asn Gly Lys Glu Tyr Lys Cys Lys Val Ser Asn Lys
                165                 170                 175

Gly Leu Pro Ser Ser Ile Glu Lys Thr Ile Ser Lys Ala Lys Gly Gln
            180                 185                 190

Pro Arg Glu Pro Gln Val Tyr Thr Leu Pro Pro Ser Gln Glu Glu Met
        195                 200                 205

Thr Lys Asn Gln Val Ser Leu Thr Cys Leu Val Lys Gly Phe Tyr Pro
    210                 215                 220

Ser Asp Ile Ala Val Glu Trp Glu Ser Asn Gly Gln Pro Glu Asn Asn
225                 230                 235                 240

Tyr Lys Thr Thr Pro Pro Val Leu Asp Ser Asp Gly Ser Phe Phe Leu
                245                 250                 255

Tyr Ser Arg Leu Thr Val Asp Lys Ser Arg Trp Gln Glu Gly Asn Val
```

```
                260                 265                 270
Phe Ser Cys Ser Val Met His Glu Ala Leu His Asn His Tyr Thr Gln
                    275                 280                 285

Lys Ser Leu Ser Leu Ser Leu Gly Lys
        290                 295

<210> SEQ ID NO 50
<211> LENGTH: 99
<212> TYPE: DNA
<213> ORGANISM: Homo sapiens

<400> SEQUENCE: 50
cacgccgacg gcagcttcag cgacgagatg aacaccatcc tggacaacct ggccgctaga    60
gacttcatca actggctgat ccagaccaag atcaccgat                          99

<210> SEQ ID NO 51
<211> LENGTH: 99
<212> TYPE: DNA
<213> ORGANISM: Artificial Sequence
<220> FEATURE:
<223> OTHER INFORMATION: GLP-2 analogue (A2G)

<400> SEQUENCE: 51
cacggcgacg gcagcttcag cgacgagatg aacaccatcc tggacaacct ggccgctaga    60
gacttcatca actggctgat ccagaccaag atcaccgat                          99

<210> SEQ ID NO 52
<211> LENGTH: 849
<212> TYPE: DNA
<213> ORGANISM: Artificial Sequence
<220> FEATURE:
<223> OTHER INFORMATION: GLP-2-hyFc8

<400> SEQUENCE: 52
cacggcgacg gcagcttcag cgacgagatg aacaccatcc tggacaacct ggccgctaga    60
gacttcatca actggctgat ccagaccaag atcaccgatg cgccggccac tacgcgcaac   120
accggccgcg gcggcgagga gaagaagaag gagaaggaga aggaggagca ggaggagcgc   180
gagaccaaga cccccgagtg ccccagccac acccagcccc tgggcgtgtt cctgttcccc   240
cccaagccca aggacaccct gatgatcagc gcacccccg aggtgacctg cgtggtcgtg    300
gatgtgagcc aggaagatcc cgaagtgcag ttcaactggt acgtggatgg cgtggaagtg   360
cacaacgcca agaccaagcc cagagaagag cagttcaact ccacctacag agtggtgagc   420
gtgctgaccg tgctgcacca ggactggctg aacggcaagg agtacaagtg caaggtgtcc   480 aacaaggcc tgcccagctc catcgagaag accatcagca agccaaagg ccagcccaga    540 gaaccccagg tgtacaccct gcctccagc caggaagaga tgaccaagaa ccaggtgtcc    600
ctgacctgcc tggtgaaagg cttctacccc agcgacatcg ccgtggagtg ggaaagcaac   660
ggccagcccg agaacaatta caagacaacc cctcccgtgc tggatagcga tggcagcttc   720
tttctgtaca gcagactgac cgtggacaag agcagatggc aggaaggcaa cgtgttcagc   780
tgcagcgtga tgcacgaagc cctgcacaac cactacaccc agaagagcct gtccctgagc   840
ctgggcaag                                                          849

<210> SEQ ID NO 53
<211> LENGTH: 864
<212> TYPE: DNA
<213> ORGANISM: Artificial Sequence
```

<220> FEATURE:
<223> OTHER INFORMATION: GLP-2-hyFc9

<400> SEQUENCE: 53

```
cacggcgacg gcagcttcag cgacgagatg aacaccatcc tggacaacct ggccgctaga      60
gacttcatca actggctgat ccagaccaag atcaccgatg ccaaggcaac gactgcgccg     120
gccactacgc gcaacaccgg ccgcggcggc gaggagaaga agaaggagaa ggagaaggag     180
gagcaggagg agcgcgagac caagaccccc gagtgcccca gccacaccca gcccctgggc     240
gtgttcctgt tccccccaa gcccaaggac accctgatga tcagccgcac cccgaggtg      300
acctgcgtgt cgtggatgt gagccaggaa gatcccgaag tgcagttcaa ctggtacgtg     360
gatggcgtgg aagtgcacaa cgccaagacc aagcccagag aagagcagtt caactccacc     420
tacagagtgg tgagcgtgct gaccgtgctg caccaggact ggctgaacgg caaggagtac     480
aagtgcaagg tgtccaacaa aggcctgccc agctccatcg agaagaccat cagcaaagcc     540
aaaggccagc cagagaacc ccaggtgtac accctgcctc ccagccagga agagatgacc      600
aagaaccagg tgtccctgac ctgcctggtg aaaggcttct accccagcga catcgccgtg     660
gagtgggaaa gcaacggcca gcccgagaac aattacaaga caacccctcc cgtgctggat     720
agcgatggca gcttctttct gtacagcaga ctgaccgtgg acaagagcag atggcaggaa     780
ggcaacgtgt tcagctgcag cgtgatgcac gaagccctgc acaaccacta cacccagaag     840
agcctgtccc tgagcctggg caag                                             864
```

<210> SEQ ID NO 54
<211> LENGTH: 891
<212> TYPE: DNA
<213> ORGANISM: Artificial Sequence
<220> FEATURE:
<223> OTHER INFORMATION: GLP-2-hyFc11

<400> SEQUENCE: 54

```
cacggcgacg gcagcttcag cgacgagatg aacaccatcc tggacaacct ggccgctaga      60
gacttcatca actggctgat ccagaccaag atcaccgatg ctcagccaca ggctgaggga     120
agcctcgcca aggcaacgac tgcgccggcc actacgcgca acaccggccg cggcggcgag     180
gagaagaaga aggagaagga gaaggaggag caggaggagc gcgagaccaa gaccccccgag    240
tgccccagcc acacccagcc cctgggcgtg ttcctgttcc ccccaagcc caaggacacc      300
ctgatgatca gccgcacccc cgaggtgacc tgcgtggtcg tggatgtgag ccaggaagat     360
cccgaagtgc agttcaactg gtacgtggat ggcgtggaag tgcacaacgc caagaccaag     420
cccagagaag agcagttcaa ctccacctac agagtggtga gcgtgctgac cgtgctgcac     480
caggactggc tgaacggcaa ggagtacaag tgcaaggtgt ccaacaaagg cctgcccagc     540
tccatcgaga agaccatcag caaagccaaa ggccagccca gagaacccca ggtgtacacc     600
ctgcctccca gccaggaaga gatgaccaag aaccaggtgt ccctgacctg cctggtgaaa     660
ggcttctacc ccagcgacat cgccgtggag tgggaaagca acggccagcc cgagaacaat     720
tacaagacaa cccctcccgt gctggatagc gatggcagct tctttctgta cagcagactg     780
accgtggaca agagcagatg gcaggaaggc aacgtgttca gctgcagcgt gatgcacgaa     840
gccctgcaca accactacac ccagaagagc ctgtccctga gcctgggcaa g              891
```

<210> SEQ ID NO 55
<211> LENGTH: 276
<212> TYPE: PRT

```
<213> ORGANISM: Artificial Sequence
<220> FEATURE:
<223> OTHER INFORMATION: GLP-1-hyFc5

<400> SEQUENCE: 55

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly Arg
            20                  25                  30

Asn Thr Gly Arg Gly Gly Glu Lys Lys Lys Glu Lys Glu Lys Glu Glu
        35                  40                  45

Glu Gln Glu Glu Arg Glu Thr Lys Thr Pro Glu Cys Pro Ser His Thr
50                  55                  60

Gln Pro Leu Gly Val Phe Leu Phe Pro Pro Lys Pro Lys Asp Thr Leu
65                  70                  75                  80

Met Ile Ser Arg Thr Pro Glu Val Thr Cys Val Val Val Asp Val Ser
                85                  90                  95

Gln Glu Asp Pro Glu Val Gln Phe Asn Trp Tyr Val Asp Gly Val Glu
                100                 105                 110

Val His Asn Ala Lys Thr Lys Pro Arg Glu Glu Gln Phe Asn Ser Thr
        115                 120                 125

Tyr Arg Val Val Ser Val Leu Thr Val Leu His Gln Asp Trp Leu Asn
    130                 135                 140

Gly Lys Glu Tyr Lys Cys Lys Val Ser Asn Lys Gly Leu Pro Ser Ser
145                 150                 155                 160

Ile Glu Lys Thr Ile Ser Lys Ala Lys Gly Gln Pro Arg Glu Pro Gln
                165                 170                 175

Val Tyr Thr Leu Pro Pro Ser Gln Glu Glu Met Thr Lys Asn Gln Val
            180                 185                 190

Ser Leu Thr Cys Leu Val Lys Gly Phe Tyr Pro Ser Asp Ile Ala Val
        195                 200                 205

Glu Trp Glu Ser Asn Gly Gln Pro Glu Asn Asn Tyr Lys Thr Thr Pro
    210                 215                 220

Pro Val Leu Asp Ser Asp Gly Ser Phe Phe Leu Tyr Ser Arg Leu Thr
225                 230                 235                 240

Val Asp Lys Ser Arg Trp Gln Glu Gly Asn Val Phe Ser Cys Ser Val
                245                 250                 255

Met His Glu Ala Leu His Asn His Tyr Thr Gln Lys Ser Leu Ser Leu
                260                 265                 270

Ser Leu Gly Lys
            275
```